(12) United States Patent
Barui et al.

(10) Patent No.: US 9,944,676 B2
(45) Date of Patent: Apr. 17, 2018

(54) CATIONIC LIPID FORMULATIONS FOR REGRESSING ESTABLISHED TUMOR

(71) Applicant: Council of Scientific & Industrial Research, New Delhi (IN)

(72) Inventors: Sugata Barui, Hyderabad (IN); Soumen Saha, Hyderabad (IN); Chaudhuri Arabinda, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 280 days.

(21) Appl. No.: 14/462,880

(22) Filed: Aug. 19, 2014

(65) Prior Publication Data

US 2016/0304558 A1    Oct. 20, 2016

(30) Foreign Application Priority Data

Aug. 19, 2013    (IN) .......................... 2442/DEL/2013

(51) Int. Cl.
| | |
|---|---|
| *A61K 9/127* | (2006.01) |
| *C07K 7/06* | (2006.01) |
| *A61K 31/713* | (2006.01) |
| *A61K 39/00* | (2006.01) |
| *C07K 1/107* | (2006.01) |
| *A61K 45/06* | (2006.01) |

(52) U.S. Cl.
CPC .............. *C07K 7/06* (2013.01); *A61K 9/1275* (2013.01); *A61K 31/713* (2013.01); *A61K 39/0011* (2013.01); *A61K 45/06* (2013.01); *C07K 1/1077* (2013.01); *A61K 2039/53* (2013.01); *A61K 2039/6018* (2013.01)

(58) Field of Classification Search
CPC .................................................... A61K 9/1275
See application file for complete search history.

(56) References Cited

PUBLICATIONS

Agemy et al (Proc Natl Acad Sci U S A. Oct. 18, 2011; 108(42): 17450-17455).*
Palomo et al (Angew. Chem. 2006, 118, 491-495).*
Avraamides C. J. et al., "Integrins in angiogenesis and lymphangiogenesis," Nat. Rev. Cancer, 8(8):604-617 (2008).
Campbell N. E., et al., "Extracellular Matrix Proteins and Tumor Angiogenesis," Journal of Oncology, 2010: 13 pages (2010).
Chen K., et al., "Integrin Targeted Delivery of Chemotherapeutics," Theranostics, 1:189-200 (2011).
Desgrosellier J. S., et al., "Integrins in cancer: biological implications and therapeutic opportunities," Nat. Rev. Cancer, 10:9-22 (2010).

(Continued)

*Primary Examiner* — Benjamin Packard
(74) *Attorney, Agent, or Firm* — Abelman, Frayne & Schwab

(57) ABSTRACT

The present invention discloses an integrin receptor targeting novel cationic CGKRK-lipopeptide. The present invention further discloses a liposomal formulation comprising the cationic CGKRK-lipopeptide, at least two co-lipids, at least one chemotherapeutic agent and a pharmaceutically acceptable carrier. The present invention also provides a method for regressing established tumors comprising administering therapeutically effective amount of the liposomal formulation comprising the chemotherapeutic agent.

18 Claims, 19 Drawing Sheets

(56) References Cited

PUBLICATIONS

Duan J., et al., "Reversion of multidrug resistance by co-encapsulation of doxorubicin and curcumin in chitosan/poly (butyl cyanoacrylate nanoparticles," International Journal of Pharmaceutics, 426:193-201 (2012).

Ferrajoli A., et al., "WP1066 Disrups Janus Kinase-2 and Induces Caspase-Dependent Apoptosis in Acute Myelogenous Leukemia Cells," Cancer Res., 67:23:11291-11299 (2007).

Folkman J., "Angiogenesis: an organizing principle for drug discovery?", Nature Rev. Drug Discover., 6(4)273-286 (2007).

Folkman J., "Tumor Angioingenesis Therapeutic Implications," The New England Journal of Medicine, 285:1182-1186 (1971).

Gabrilovich D., "Mechanisms and Functional Significance of Tumour-Induced Dendritic-Cell Defects," Nature Ref. Immunol., 4:941-952 (2004).

Gurunathan S., et al., "DNA Vaccines: Immunolgoy, Applicaiton, and Optimization," Annu. Rev. Immunol., 18:927-974 (2000).

Ishii, K. J., et al., "TANK-binding kinase-1 delineates innate and adaptive immune responses to DNA vaccines," Nature, 471:725-729 (2008).

Kuldo J. M., et al., "Molecular Pathways of Endothelial Cell Activation for (Targeted) Pharmacological Intervention of Chornic Inflammatory Diseases," Current Vascu7lar Pharmacology, 3:11-39 (2005).

Niu G., et al., "Constitutive Stat3 activity up-regulates VEGF expression and tumor angiogenesis," Oncogene, 21:2000-2008 (2002).

Pramanik D., et al., "Lipopeptide with a RGK Tetrapeptide Sequence Can Selectively Target Genes to Proangiogenic a5B1 Integrin Receptor and Mouse Tumor Vasculature," J. Med. Chem., 51:7298-7302 (2008).

Sallusto F., et al., "Dendritic Cells Use Macropinocytosis and the Mannose Receptor to Concentrate Macromolecules in the Major Histocompatibility Complex Class II Compartment: Downregulation by Cytokines and Bacterial Products," J. Exp. Med., 182:389-400 (1995).

Samanta S., et al., "The use of RGDGWK-lipopeptide to selectively deliver genes to mouse tumor vasculature and its complexation with p53 to inhibit tumor growth," Biomaterials, 31:1787-1797 (2010).

Shukla G. S., et al., "Selective delivery of therapeutic agents for the diagnosis and treatment of cancer," Expert Opin. Biol. Ther., 6:39-54 (2006).

Srinivas R., et al., "Cationic Amphiphile with Shikimic Acid Headgroup Shows More Systemic Promise Than Its Mennosyl Analogue as DNA Vaccine Carrier in Dendritic Cell Based Genetic Immunization," J. Med. Chem., 53:1387-1391 (2010).

Szakacs G., et al., "Targeting multidrug resistance in cancer," Nature Reviews Drug Discovery, 5:219-234 (2006).

Timofeeva O. A., et al., "STAT3 suppresses transcription of proapoptotic genes in cancer cells with the involvement of its N-terminal domain," PNAS, 110:4:1267-1272 (2013).

Un K., et al., "Suppression of Melanoma Growth and Metastasis by DNA Vaccination Using an Ultrasound-Responsive and Mannose-Modified Gene Carrier," Mol. Pharm., 8:543-554 (2011).

Un K., et al., "Development of an ultrasound-responsive and mannose-modified gene carrier for DNA vaccine therapy," Biomaterials, 31:7813-7826 (2010).

Wadajkar A. S., et al., "Multifunctional particles for melanoma-targeted drug delivery," Acta. Biomateralia, 8:2996-3004 (2012).

* cited by examiner

```
                        SEQUENCE LISTING

<160> NUMBER OF SEQ ID NOS: 5

<210> SEQ ID NO 1
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 1

Cys Gly Lys Arg Lys
1               5

<210> SEQ ID NO 2
<211> LENGTH: 18
<212> TYPE: DNA
<213> ORGANISM: Artificial Sequence
<220> FEATURE:
<223> OTHER INFORMATION: Mouse STAT3 Forward Primer

<400> SEQUENCE: 2
acccaacagc cgccgtag                                                  18

<210> SEQ ID NO 3
<211> LENGTH: 24
<212> TYPE: DNA
<213> ORGANISM: Artificial Sequence
<220> FEATURE:
<223> OTHER INFORMATION: Mouse STAT3 Reverse Primer

<400> SEQUENCE: 3
cagactggtt gtttccattc agat                                           24

<210> SEQ ID NO 4
<211> LENGTH: 4
<212> TYPE: PRT
```

```
<213> ORGANISM: Artificial Sequence
<220> FEATURE:
<223> OTHER INFORMATION: Synthetic Peptide

<400> SEQUENCE: 4

Arg Gly Asp Lys
1

<210> SEQ ID NO 5
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 5

Arg Gly Asp Gly Trp Lys
1               5
```

CATIONIC LIPID FORMULATIONS FOR REGRESSING ESTABLISHED TUMOR

This application claims priority from Indian patent application No. 2442/DEL/2013, filed Aug. 19, 2013, which is incorporated by reference in its entirety.

FIELD OF THE INVENTION

The present invention relates to a novel liposomal formulation comprising a cationic lipopeptide having a CGKRK-penta peptide head-group, co-lipids, and chemotherapeutic agents. The present invention also relates to a method for regressing established tumor by administering the liposomal formulation.

BACKGROUND AND PRIOR ART OF THE INVENTION

Tumor-specific delivery of drugs for diagnosis and treatment of cancer is an active area of investigations in both experimental and clinical trials (Shukla, G. S. et al. Expert. Opin. Biol. Ther. 2006; 6:39-54). Receptors over expressed on tumor cells or tumor endothelial cells are often exploited for killing tumor cells by selective delivery of potent cytotoxic drugs to either tumor or tumor vasculatures or both (Vyas, S. P. et al. Crit. Rev. Ther. Drug Carrier Syst. 2001; 18:1-76). Examples of such receptors are integrin receptors and $\alpha/\beta$ heterodimeric transmembrane glycoprotein receptors (the primary cell-adhesion molecules). These receptors are over expressed on the surface of tumor endothelial cells and many tumor cells whereas their degree of expression in pre-existing resting endothelial cells and normal tissues is minimal (Desgrosellier, J. S. Nat. Rev. Cancer 2010; 10:9-22). Because of these reasons, integrin receptor mediated delivery of potent cytotoxic drugs/genes to tumors and tumor endothelial cells is an emerging therapeutic approach for inhibiting tumor growth (Kuldo, J. M. et al. Current Vascular Pharmacology 2005; 3:11-39). For instance, recent studies have shown that integrin targeted RGD-functionalized nanoparticles can deliver anti-cancer drugs selectively to tumor sites (Aniket, S. et al. Acta Biomaterialia 2012; 8:2996-3004, Danhier, F. et al. J. Control Release. 2009; 140:166). Lipopeptides containing a non-cyclic, conformationally unstained simple RGDK and RGDGWK peptide sequence in their polar head-group region can also selectively target genes to tumor vasculature via proangiogenic $\alpha5\beta1$ integrin receptors (Pramanik, D. et al. J. Med. Chem. 2008; 51:7298-7302, Samanta, S. et al. Biomaterials. 2010; 31:1787-1797). Combination of potent chemotherapeutics is often recommended toward enhancing therapeutic efficacies, minimizing drug resistance and alleviating toxic side effects (Jinghua, D. et al. International Journal of Pharmaceutics 2012; 426:193-201). Besides chemotherapy, antiangiogenic cancer therapy is another very promising therapeutic modality for combating cancer. Folkman proposed the concept of anti-angiogenic cancer therapy more than forty years back (Folkman, J. N. Engl. J Med. 1971; 285:1182-1186). Angiogenesis, the sprouting of new blood vessels from pre-existing vessels, is a remarkable feature of tumor growth (Carmeliet, P. Nature, 2005; 438:932). Growing tumors get their oxygen and nutrients from these tumor neovasculatures (newly formed blood vessels around tumor). Folkman envisaged for the first time that inhibition of angiogenesis (i.e. killing of tumor endothelial cells) would shut down oxygen and nutrient supply to tumor cells and in consequence, the tumor cells will die of starvation. Prior study showed that the transcription factor STAT3 (signal transducer and activator of transcription 3) plays pivotal role in angiogenesis through modulating VEGF expression (Niu, G. et al. Oncogene 2002; 21:2000-2008). It also produces immunosuppressive factors such as VEGF, TGFβ, IL-6, IL-10 which, in turn, negatively affect functional maturation of dendritic cells, body's most professional antigen presenting cells (APCs) (Gabrilovich, D. et al. Nature Rev. Immunol. 2004; 4:941-952; Zou, W. Nature Rev. Cancer 2005; 5:263-274). Since angiogenesis, sprouting of new blood vessels (neovasculatures) from existing vessels, is a distinguishing feature of growing tumors, inhibiting tumor-associated angiogenesis is a promising therapeutic modality to combat cancer (Weis, S. M. et al. Nature Medicine 2011; 17:1359-70). Tumor stroma primarily consisting of various extracellular matrix (ECM) components is a key regulator of angiogenic cascade (Campbell, N. E. et al. J. Oncol. 2010; 2010:586905). Sprouting of tumor neovasculature critically depends on the interactions between the various ECM components in the tumor stroma and the integrin receptors, the $\alpha/\beta$ heterodimeric transmembrane glycoprotein receptors (the primary cell-adhesion molecules) expressed on the surface of tumor endothelial cells (Desgrosellier, J. S. et al. Nat. Rev. Cancer 2010; 10:9-22, Folkman, J. Nat. Rev. Drug Discov. 2007; 6(4):273-86, Avraamides, C. J. Nat. Rev. Cancer 2008; 8(8):704-17). An elegant strategy for targeting potent anti-cancer drugs/genes selectively to tumor vasculatures is based on identifying high-affinity integrin receptor ligands through use of phage display libraries under in vivo conditions. Integrins receptor can be internalized by cells on activation with anchoring ligands thereby significantly facilitating the delivery of chemotherapeutics into neoplastic cells and leukocytes when such chemotherapeutics are associated with high affinity ligands for various integrin receptors (Chen, K. et al. Theranostics 2011; 1:189-200). More specifically, immunosuppressive factors inhibit DC maturation by inhibiting expression of MHC class II, co-stimulatory molecules CD80 & CD86 and immune-stimulating molecules, such as tumor-necrosis factor (TNF) and IL-12 (Yu, H. et al. Nature Rev. Immunol. 2007; 7:41-51; Yu, H. et al. Nature Rev. Cancer 2009; 9:798-809). Hence, inhibiting STAT3 signaling pathway is an attractive therapeutic approach for most types of human cancers. WP1066, one of the potent commercially available inhibitors of JAK-STAT pathway, inhibits proliferation and induces apoptosis of cancer cells (Ferrajoli, A. et al. Cancer Res. 2007; 67:11291-11299, Verstovsek, S. et al. Clin. Cancer Res. 2008; 14:788-796). Another efficient method of inhibiting stat3 signaling pathway is based on cleaving stat3mRNA in RNA interference pathway by small non-coding stat3-siRNA (Timofeeva, A. O. et al. PNAS 2013; 110:1267-1272). DNA vaccination, the administration of tumor antigen encoded DNA (capable of inducing both humoral and cellular immune responses), is an emerging therapeutic approach for treatment of cancer (Ishii, K. J. et al. Nature 2008; 451:725-729, Gurunathan, S. et al. Annu. Rev. Immunol. 2000; 18:927-974). A promising approach for enhancing the efficacy of DNA vaccination is based on targeting DNA vaccines to recipients' APCs via mannose receptor, a 180 kDa multi-domains unique transmembrane receptor expressed on the cell surfaces of APCs (Sallusto, F. et al. J. Exp. Med. 1995; 182:389-400). Previously Srinivas, R. et al. demonstrated that liposomes of cationic amphiphiles with mannose-mimicking quinic and shikimic acid head-groups can target DNA vaccines to APCs via mannose receptors by forming electrostatic complexes (lipoplexes) of plasmid DNA encoding melanoma tumor associated antigen (MART1) (Srinivas, R. et al. J. Med. Chem. 2010; 53:1387-1391). Subsequently, Srinivas, R. et al. disclosed development of mannose receptor specific lysinylated cationic amphiphiles with mannose-mimicking shikimic and quinic acid head-groups for use in dendritic cell based genetic immunization (Srinivas, R. et al. Indian Patent Application No. 2170/DEL/2010).

However, there are a number of time-consuming and cost-ineffective steps to be followed in such ex vivo (outside the body cells) DC-transfection based genetic immunization processes. The process involves painstaking isolation of autologous DCs, transfecting them ex vivo with tumor antigen encoded DNA vaccines and reimplanting the ex vivo transfected DCs back into the recipient's body. To this end, Hashida and coworkers reported development of mannose-receptor selective and ultrasound-responsive mannosylated liposomes for direct in vivo transduction of DCs in genetic immunization (Un K. et al. Biomaterials 2010; 31: 7813-7826; Un K. et al. Mol Pharm 2011; 8: 543-554). Most recently, Garu, A. et al. has disclosed that direct in vivo immunization of mice with electrostatic complexes (lipoplexes) of p-CMV-gp100 and p-CMV-tyrosinase (DNA vaccines encoding melanoma tumor antigens gp-100 & tyrosinase, respectively) and liposome of lysinylated cationic amphiphiles with both guanidine and mannose-mimicking shikimic acid head-groups is capable of providing long-lasting (100 days post tumor challenge) tumor protection against aggressive melanoma tumor challenge in immunized mice (Indian Patent Application No. 0017/DEL/2013). Although inhibiting growth of melanoma tumor in mice priorly immunized with such direct in vivo DC-targeting liposomal DNA vaccine formulation was possible, this approach failed to regress established tumor.

Anticancer drugs commonly used for treating several malignant tumors unfortunately are also associated with multidrug resistance (MDR), acute toxicities, cumulative dose-limiting cytoxicity, etc. Thus, there is an urgent need to use combination of chemotherapeutics toward alleviating chemoresistance and improving drug-efficacy (Szakacs, G. et al. Nat. Rev. Drug Discov. 2006; 5:219-234).

OBJECTIVE OF THE INVENTION

The main object of the present invention is to provide a novel lipopeptide having CGKRK-penta peptide head-group. Another object of the present invention is to provide a process for the synthesis of the integrin receptor targeting CGKRK-lipopeptide.

Yet another object of the present invention is to provide a liposomal formulation comprising a cationic lipopeptide having CGKRK-penta peptide head-group, co-lipids, and chemotherapeutic agents.

Still another objection of the present invention is to provide a method for regressing established tumor by administering the liposomal formulation.

Another objection of the present invention is to provide a method delivery of the liposomal formulation for the regressing established tumor.

SUMMARY OF THE INVENTION

The present invention relates to a cationic lipopeptide having formula A.

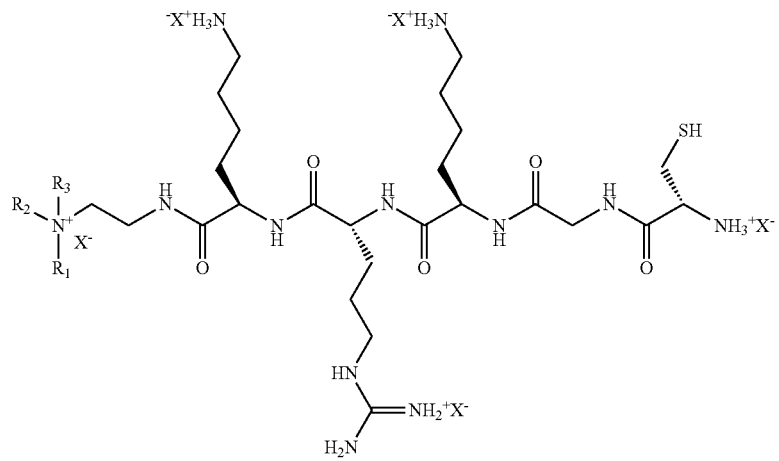

Formula A

Wherein, the sequence of peptide is CGKRK;

$R_1$ and $R_2$ are each independently selected from hydrogen or a lipophilic moiety containing eight to twenty four carbon atoms selected from the group consisting of alkyl, mono-, di- and tri-unsaturated alkenyl, provided both $R_1$ and $R_2$ are not hydrogen;

$R_3$ is selected from the group consisting of hydrogen, $C_1$-$C_5$alkyl, hydroxy and $C_1$-$C_5$ amino-alkyl; and X is either chlorine or bromine.

In an embodiment of the present invention, the cationic lipopeptide having formula A is represented by cationic CGKRK-lipopeptide 1.

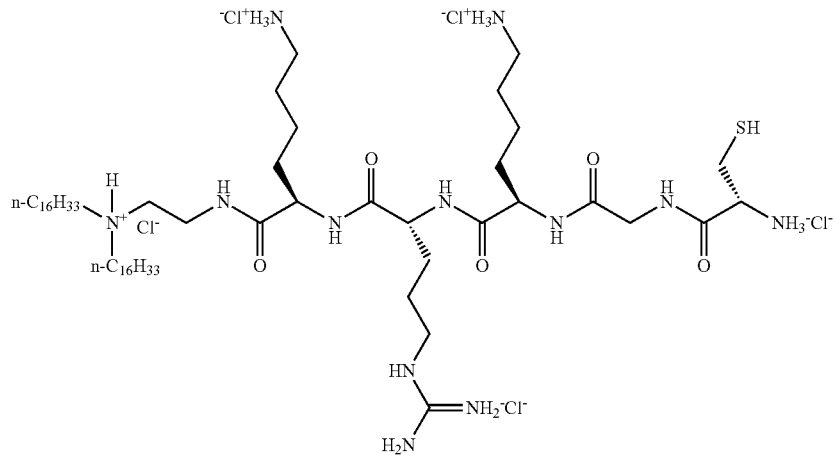

Cationic CGKRK-lipopeptide 1

In another embodiment of the present invention, the cationic lipopeptide containing integrin receptor targeting CGKRK-lipopeptide A can be used in pure form or in combination with co-lipid.

An embodiment of the present invention provides a process for preparation of the lipopeptide, said process comprising the steps:

i. coupling Fmoc-Arg(Pbf)-OH with H-Lys(BOC)-2-Cl-Trt resin using HATU and DIPEA in DMF at room temperature for 1.5 hour to obtain an intermediate 2

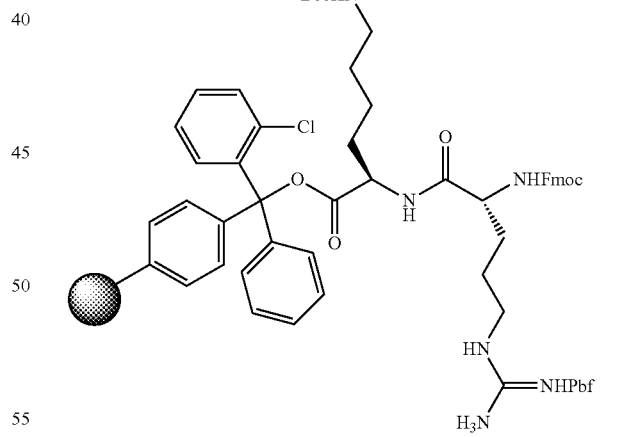

Intermediate 2 ii. removing the Fmoc group from intermediate 2 by washing with piperidine in DMF at room temperature;

iii. sequential couplings of Fmoc-Lys(Boc)-OH, Fmoc-Gly-OH and BOC-Cys(Trt)-OH using HATU and DIPEA(4 eqv.) to intermediate of step (ii) using the condition of step (i) to obtain a penta peptide intermediate 3;

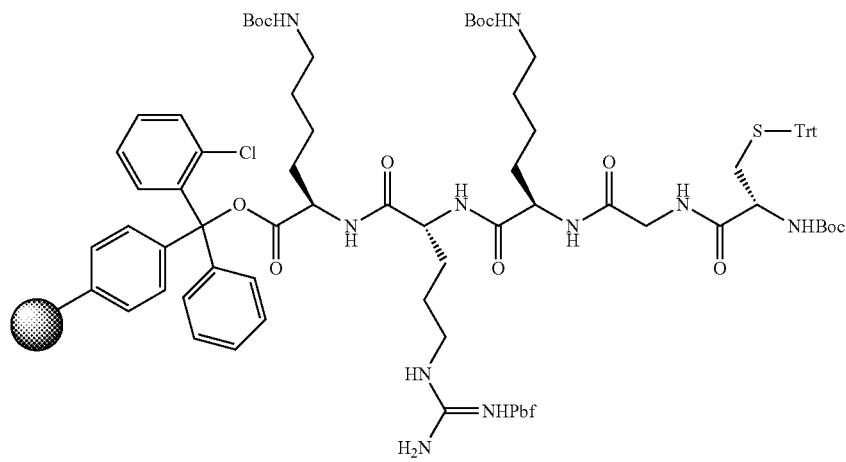

Penta peptide intermediate 3 iv. removing the resin bound to penta peptide intermediate 3 obtained in step (iii) followed by treatment with TFA:DCM (1:2 by v/v) for 2 hours at 0° C. to obtain a protected penta peptide intermediate 4;

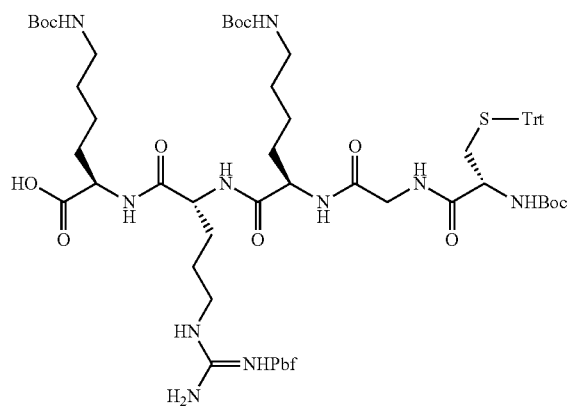

Penta peptide intermediate 4 v. coupling the protected penta peptide intermediate 4 obtain in step (iv) with N,N-di-n-hexadecyl-N-2-aminoethylamine in dry DCM to obtain a protected CGKRK-lipopeptide;

vi. deprotecting the CGKRK-lipopeptide obtained in step (v) with TFA-Thioanisole-EDT-TIS to obtain a deprotected CGKRK-lipopeptide; and vii. purifying the CGKRK-lipopeptide obtained in step (vi) to obtain the CGKRK lipopeptide A.

Another embodiment of the present invention provides a liposomal formulation comprising the cationic CGKRK-lipopeptide having formula A, at least one chemotherapeutic agent, at least two co-lipids and a pharmaceutically acceptable carrier.

In an embodiment of the present invention, there is provided a liposomal formulation, wherein the co-lipids are selected from the group consisting of a neutral phosphatidyl ethanolamine, neutral phosphatidyl choline, phosphatidylphosphocholine, phosphatidylglycerol, cholesterol and a di-cationic amphiphile.

In an embodiment of the present invention there is provided a liposomal formulation, wherein the di-cationic amphiphile is selected from the group consisting of n-$C_{14}H_{29})_2N^+(CH_3)CH^2CH_2N^+(C_3)_32Cl^-$, (n-$C_{16}H_{33})_2N^+(CH_3)CH_2CH_2N^+(CH_3)_3$ 2Cl$^-$, and (n-$C_{18}H_{37})_2N^+(CH_3)CH_2CH_2N^+(CH_3)_32Cl^-$.

In an embodiment of the present invention there is provided a liposomal formulation, wherein the pharmaceutically acceptable carrier is selected from the group consisting of di-oleoylphosphatidylcholine, di-stearoylphosphatidylcholine, di-oleoylphosphoethanolamine.

In an embodiment of the present invention, there is provided a liposomal formulation wherein the weight ratio of cationic CGKRK-lipopeptide having formula A: co-lipid: chemotherapeutic agent is in the range of 1-3.0:0.5-3.0:0.5-2.0.

In another embodiment of the present invention there is provided a liposomal formulation, wherein the molar ratio of cationic CGKRK-lipopeptide having formula A: di-cationic amphiphile:cholesterol in the formulation is in the range of 0.1-1:0.5-3.0:0.1-2.0.

In another embodiment of the present invention there is provided a liposomal formulation, wherein the chemotherapeutic agent is selected from the group consisting of a STAT3 inhibitor, a protein, a nucleic acid, an oligonucleotide and a peptide or a combination thereof.

In another embodiment of the present invention there is provided a liposomal formulation, wherein the nucleic acid is a siRNA.

In another embodiment of the present invention there is provided a liposomal formulation, wherein the chemotherapeutic agent is selected from the group consisting of a STAT3 inhibitor III and a stat3 siRNA or a combination thereof.

In another embodiment of the present invention there is provided a liposomal formulation, wherein the formulation is administered by a mode selected from the group consisting of cutaneous, sub-cutaneous, intradermal, nasal, intravenous, intramuscular, intraperitonial and pulmonary route.

In another embodiment of the present invention there is provided a liposomal formulation, wherein the weight ratio of STAT3 inhibitor III and stat3 siRNA is in the range of 5-20:1-5 when used in combination.

An embodiment of the present invention provides a method of treating cancer comprising administering an effective amount of the liposomal formulation to a subject in need thereof.

In an embodiment of the invention there is provided a method of treating cancer, wherein the formulation induces apoptosis and inhibits stat3-phosphorylation in both endothelial cells and tumor cells.

In an embodiment of the invention there is provided a method of treating cancer, wherein the formulation shows synergistic effect of the chemotherapeutic agent to inhibit tumor growth via apoptosis of tumor endothelial cells and apoptosis of tumor cells.

An embodiment of the present invention provides a liposomal formulation, wherein the formulation comprises the cationic CGKRK-lipopeptide having formula A, a STAT3 inhibitor III, a di-cationic amphiphile, cholesterol and a pharmaceutically acceptable carrier.

An embodiment of the present invention provides a liposomal formulation, wherein the formulation comprises the cationic CGKRK-lipopeptide having formula A, a stat3 siRNA, a di-cationic amphiphile, cholesterol and a pharmaceutically acceptable carrier.

An embodiment of the present invention provides a liposomal formulation, wherein the formulation comprises the cationic CGKRK-lipopeptide having formula A, a STAT3 inhibitor III, a stat3siRNA, a di-cationic amphiphile, cholesterol and a pharmaceutically acceptable carrier.

An embodiment of the present invention provides a method of delivery of liposomal formulation selectively to tumor cells and tumor endothelial cells comprising administering the liposomal formulation comprising the cationic CGKRK-lipopeptide having formula A, at least one chemotherapeutic agent and at least two co-lipids to a subject in need thereof.

In an embodiment of the present invention, there is provided a method of delivery of liposomal formulation selectively to tumor cells and tumor endothelial cells, wherein the chemotherapeutic agent is selected from the group consisting of a STAT3 inhibitor II and a stat3siRNA or a combination thereof.

In an embodiment of the present invention, there is provided a method of delivery of liposomal formulation selectively to tumor cells and tumor endothelial cells, wherein the subject is a human.

In an embodiment of the present invention, there is provided a method of delivery of liposomal formulation selectively to tumor cells and tumor endothelial cells, wherein the chemotherapeutic drug is selectively delivered to the tumor cells and tumor endothelial cells via an integrin receptor selected from the group consisting of $\alpha v \beta 3$, $\alpha v \beta 5$ and $\alpha 5 \beta 1$ or a combination thereof.

In an embodiment of the present invention, there is provided a method of delivery of liposomal formulation selectively to tumor cells and tumor endothelial cells, wherein the liposomal formulation comprises cationic CGKRK-lipopeptide having formula A which acts as an integrin receptor binding agent.

In an embodiment of the present invention, there is provided a method of delivery of liposomal formulation selectively to tumor cells and tumor endothelial cells, wherein the liposomal formulation is delivered by a mode of administration selected from the group consisting of cutaneous, sub-cutaneous, intradermal, nasal, intravenous, intramuscular, intraperitonial and pulmonary route.

BRIEF DESCRIPTION OF THE DRAWINGS

FIG. 2A shows untreated cells. FIG. 2B shows cells treated with WP1066 solubilized in liposome of CGKRK-lipopeptide 1. FIG. 2C shows cells treated with stat3-siRNA encapsulated in liposome of CGKRK-lipopeptide 1. FIG. 2D shows cells treated with both WP1066 & stat3-siRNA co-encapsulated in liposome of CGKRK-lipopeptide 1.

FIG. 3A shows that tumor vasculature targeting liposomes of CGKRK-lipopeptide 1 encapsulating only WP1066 and only stat3 siRNA were found to be significantly (by 2-3 folds) less efficient in inhibiting melanoma tumor growth in syngeneic mice when compared to degree of tumor growth inhibition observed with intravenously administered WP 1066 & stat3siRNA both co-encapsulated in liposomes of CGKRK-lipopeptide 1. FIG. 3B provides the image of representative samples of B16F10 tumors excised on day 24 after tumor inoculation. FIG. 3C shows that the TUNEL-positive cells (i.e. cells undergoing apoptosis) were found to be co-localized with tumor endothelial cells across the entire cryosections.

The values 1, 2, 3, 4, 5, 6 represent lanes. Lane 1, untreated cells; lane 2, cells treated with targeted liposomal WP1066; lane 3, cells treated with targeted liposome containing STAT3siRNA; lane 4, cells treated with targeted liposome containing both WP1066 and STAT3siRNA; lane 5, cells treated with targeted liposome containing scrambled siRNA; lane 6, cells treated with targeted liposome containing both WP1066 and scrambled siRNA. FIG. 4A shows the mRNA level of VEGF, stat3, Bcl2, BclX$_L$ and caspase3 genes in untreated and treated B16F10 cells. FIG. 4B shows the amount of stat3 and p-stat3 at protein level in untreated and treated B16F10 cells. FIG. 4C shows the amount of stat3 and p-stat3 at protein level in untreated and treated tumor cells.

FIG. 5A shows the regression of established tumor through combined use of targeted chemotherapy and genetic immunization. FIG. 5B shows the survivability study.

ABBREVIATIONS

Figure 1A:
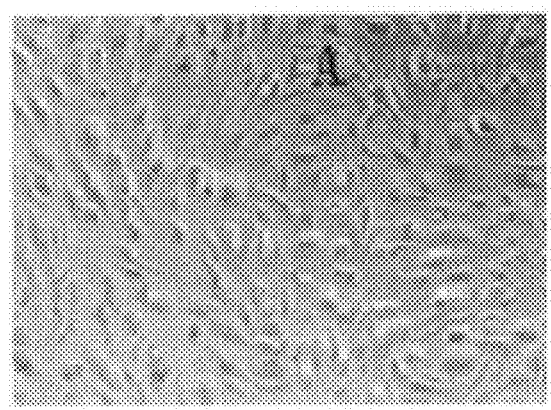
FIG. 1A shows a bright field image of HUVEC control cells without antibody pretreatment, taken 3 hours after addition of the liposomes of the present invention.
Figure 1B:
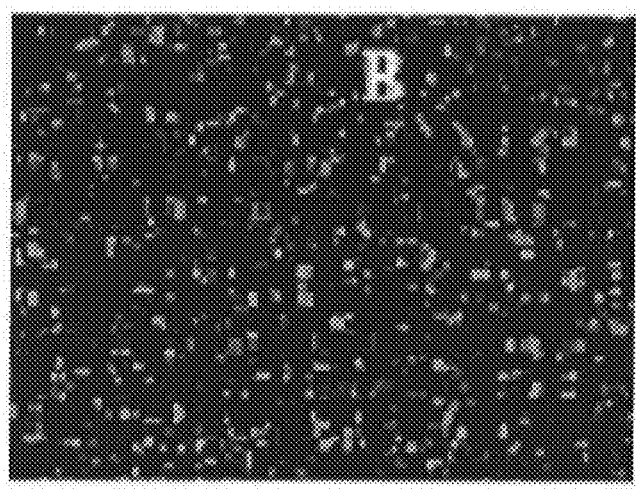
FIG. 1B shows uptake of FITC labelled siRNA by the cells of FIG. 1A.
Figure 1C:
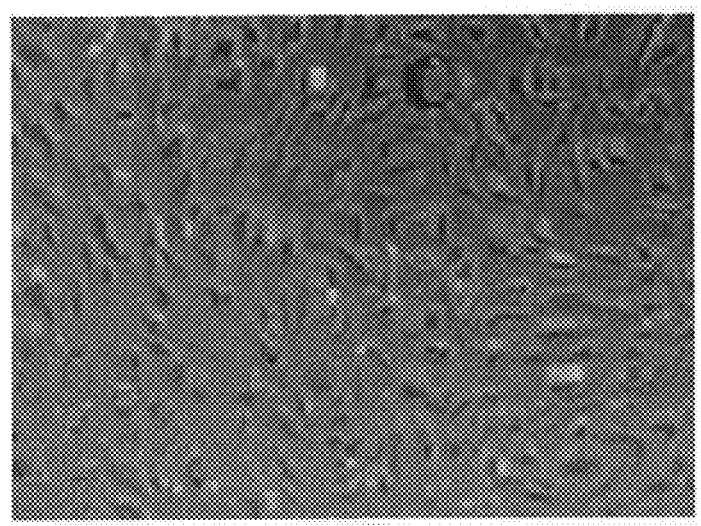
FIG. 1C is a merge of FIGS. 1A and 1B.
Figure 1D:
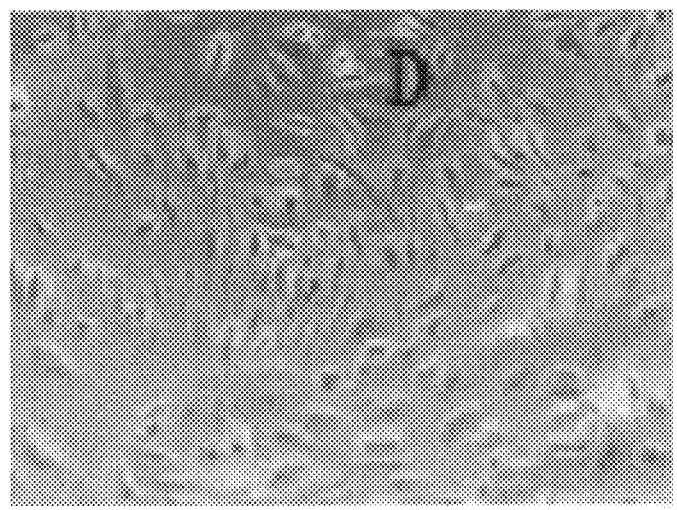
FIG. 1D shows a bright field image of HUVEC control cells pretreated with a monoclonal antibody against $\alpha 5 \beta 1$ integrin receptors, taken 3 hours after addition of the liposomes of the present invention.
Figure 1E:
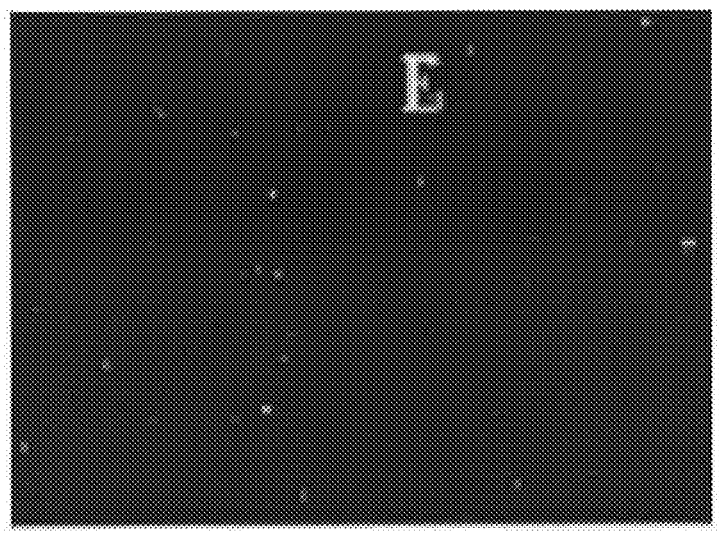
FIG. 1E shows uptake of FITC labelled siRNA by the cells of FIG. 1D.
Figure 1F:
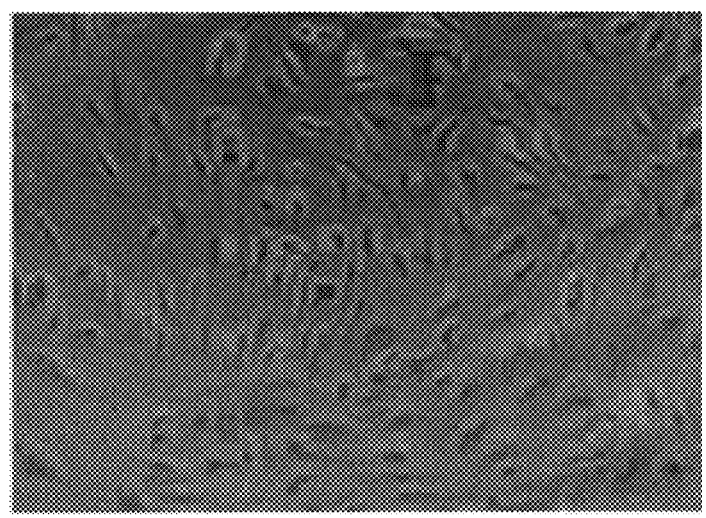
FIG. 1F is a merge of FIGS. 1D and 1E.
Figure 1G:
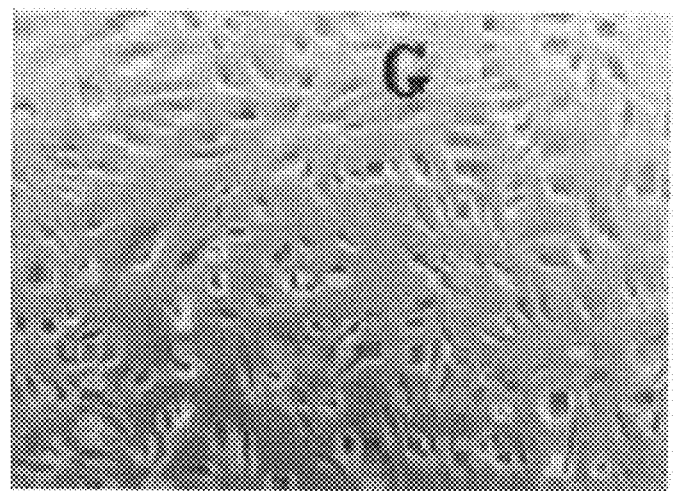
FIG. 1G shows a bright field image of HUVEC control cells pretreated with a monoclonal antibody against $\alpha v \beta 3$ integrin receptors, taken 3 hours after addition of the liposomes of the present invention.
Figure 1H:
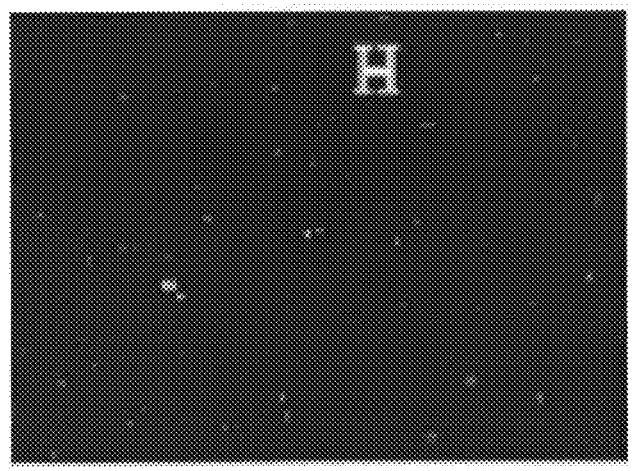
FIG. 1H shows uptake of FITC labelled siRNA by the cells of FIG. 1G.
Figure 1I:
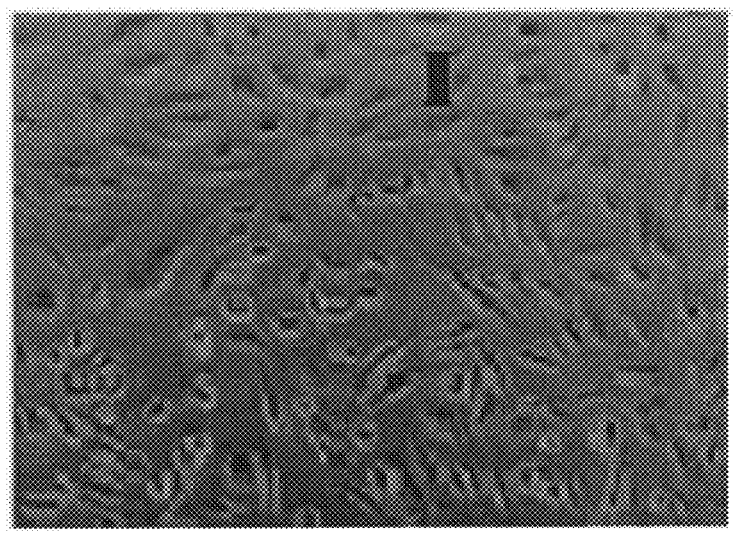
FIG. 1I is a merge of FIGS. 1G and 1H.
Figure 1J:
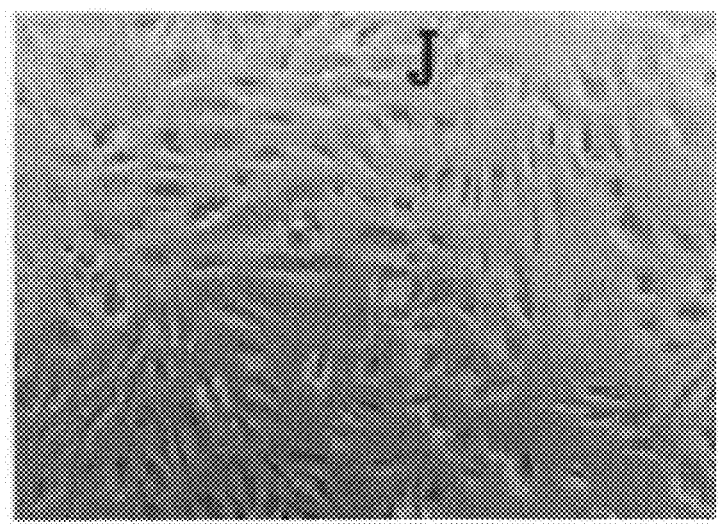
FIG. 1J shows a bright field image of HUVEC control cells pretreated with a monoclonal antibody against $\alpha v \beta 5$ integrin receptors, taken 3 hours after addition of the liposomes of the invention.
Figure 1K:
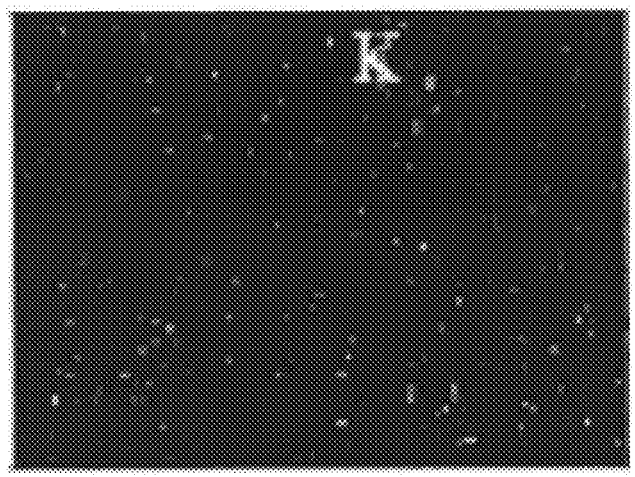
FIG. 1K shows uptake of FITC labelled siRNA by the cells of FIG. 1J.
Figure 1L:
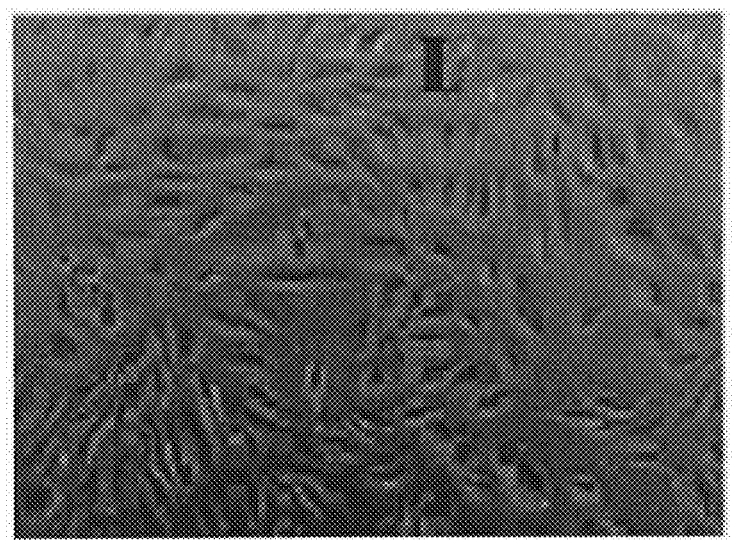
FIG. 1L is a merge of FIGS. 1J and 1K.
Figure 2A:
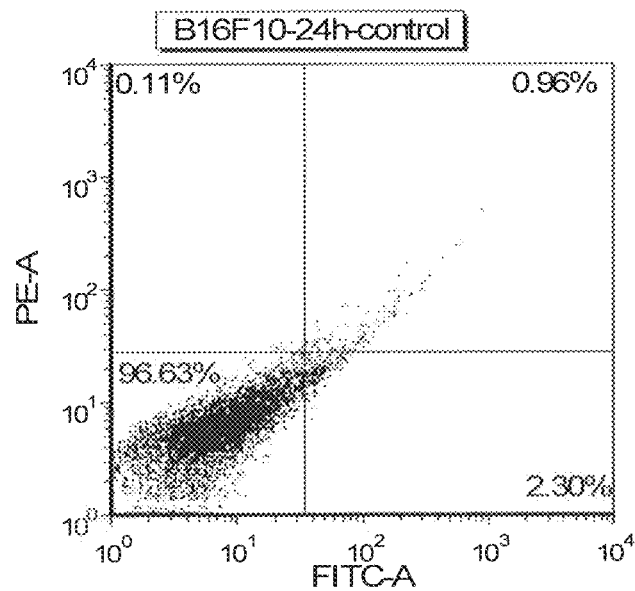
FIGS. 2A-2D show that treatment with liposomally co-encapsulated stat3siRNA and WP1066 shows synergic effect in inducing apoptosis in melanoma tumor cells (B16F10).
Figure 2B:
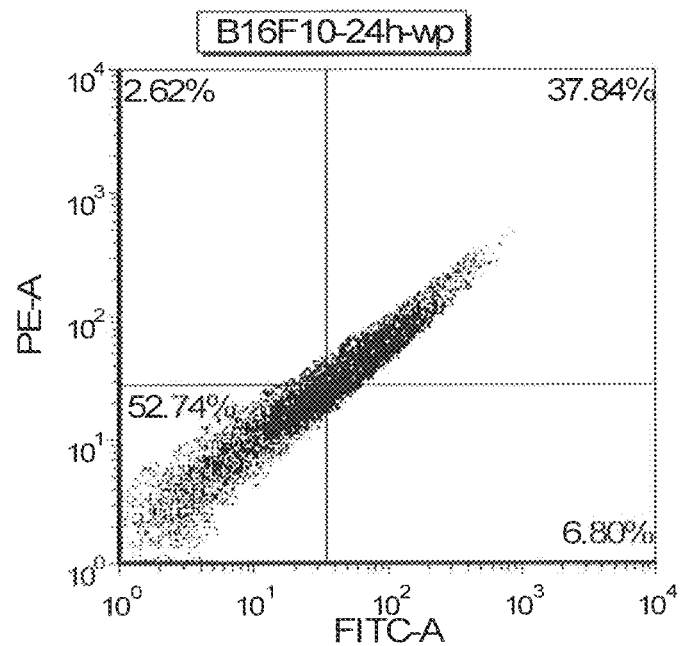
Figure 2C:
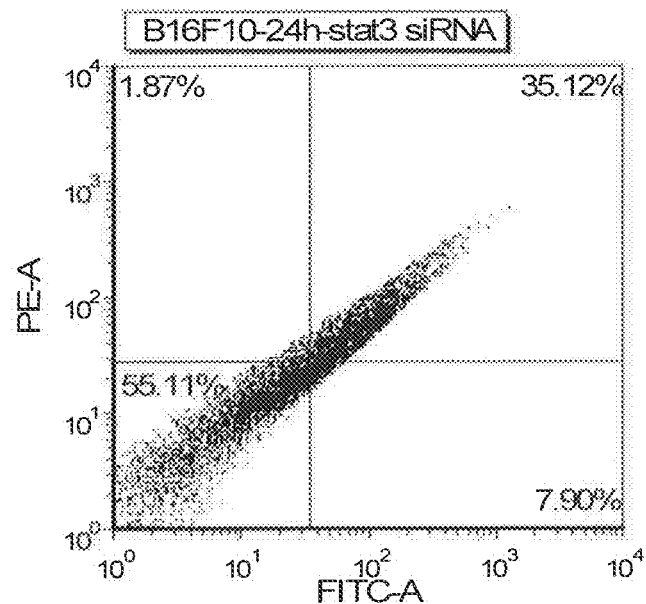
Figure 2D:
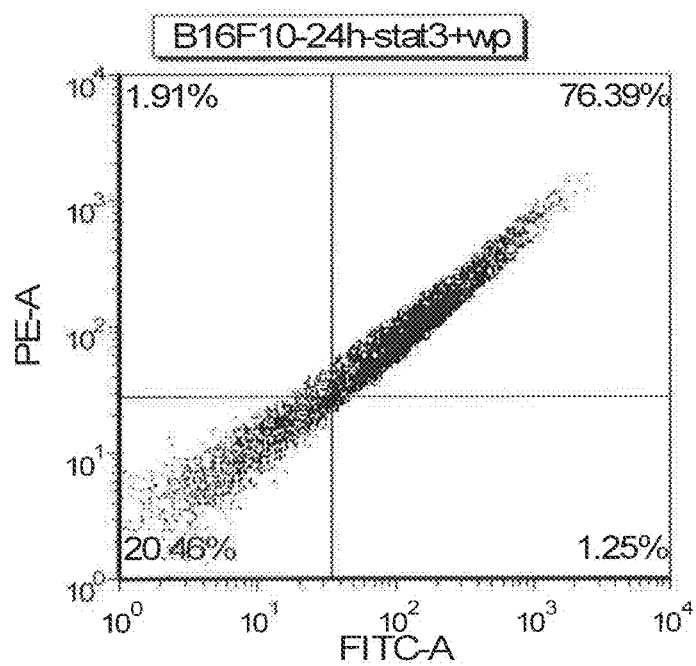

CGKRK—Cysteine Glycine Lysine Arginine Lysine
HUVEC—Human Umbilical Vein Endothelial Cells
C57BL/6J—is a common inbred strain of laboratory mouse
vWF—Von Willebrand Factor
APC—Antigen presenting cell
MART1—Melanoma associated antigen recognized by T-cells
STAT—Signal transducer and activator of transcription
JAK—Janus kinase
TNF—Tumor necrosis factor
IL—Interleukin
DC—Dendritic cell
DNA—Deoxyribonucleic acid
siRNA—small interfering ribonucleic acid
miRNA—micro ribonucleic acid
gp—glycoprotein
pCMV—plasmid cytomegalovirus
WP—1066 Commercially available JAK inhibitor
HATU—1-[Bis(dimethylamino)methylene]-1H-1,2,3-triazolo[4,5-b]pyridinium 3-oxid hexafluorophosphate
HOBT—Hydroxybenzotriazole
DIPEA—N,N-Diisopropylethylamine
EDCI—1-Ethyl-3-(3-dimethylaminopropyl)carbodiimide
TIS—Triisopropylsilane
TFA—Trifluoroacetic acid
DCM—Dichloromethane
DMEM—Dulbecco modified Eagle's minimal essential medium
EBM2—Endothelial basal medium
FBS—Fetal bovine serum

DETAILED DESCRIPTION OF THE INVENTION

The present invention discloses that liposomes of lipopeptide containing tumor homing peptide sequence CGKRK can deliver drugs or genes to endothelial and tumor cells via all the three widely used $\alpha v\beta 3$, $\alpha v\beta 5$ and $\alpha 5\beta 1$ integrin receptors.

The present invention discloses that intravenous administration of stat3-siRNA and WP1066 (a known inhibitor of stat3 phosphorylation; STAT3 inhibitor III) both coencapsulated in the liposomal formulation of the CGKRK-lipopeptide A shows synergic effect and inhibits tumor growth significantly in a syngenic mouse tumor model presumably through inducing apoptosis of tumor vasculatures. Inhibition of stat3 phosphorylation by using stat3 siRNA and WP1066 (STAT3 inhibitor III) can enhance antitumor immune responses in tumor microenvironment. Degree of tumor growth inhibition can be further enhanced with simultaneous use of other potent immunotherapeutic agents such as cancer vaccines. A promising approach for enhancing the efficacy of DNA vaccination is based on targeting DNA vaccines to APCs via mannose receptor. The present invention discloses that along with targeted delivery of multiple chemotherapeutics (stat3-siRNA and WP1066) to tumor vasculature, simultaneous immunization (after two weeks post tumor inoculation i.e. on therapeutic mode not on usual preventive mode) with electrostatic complexes (lipoplexes) of DNA vaccines p-CMV-Mart1 (encoding melanoma tumor antigen Mart1) and direct in-vivo DC-targeting liposomes of lysinylated cationic amphiphiles with both guanidine and mannose-mimicking shikimoyl head-groups can regress even established tumor.

The present invention also relates to a process for the synthesis of the novel cationic lipopeptide with integrin targeting head-group. The present invention further discloses integrin receptor mediated combined siRNA and drug delivery properties of the liposome of the cationic CGKRK-lipopeptides A. The novel structural feature of the cationic lipopeptide with integrin targeting CGKRK-head-group disclosed in the present invention include: (1) presence of hydrophobic groups which are directly linked to the positively charged nitrogen atom and (2) presence of integrin receptor binding polar CGKRK peptide head-group covalently linked to nitrogen atom through ethylene functionality. It is believed that this unique structural feature contributes significantly to combined siRNA and drug delivery efficiency of the cationic lipopeptide containing the integrin targeting CGKRK head-groups. According to the practice of the present invention, "cationic" means the positive charge is either on quaternized nitrogen or on a protonated nitrogen atom. The cationic characters of the present lipopeptide contributes to the enhanced interaction of the lipopeptide with biologically active molecules such as nucleic acids and/or with cell constituents such as plasma membrane glycoproteins. Such enhanced interaction between the cationic lipopeptide and the therapeutically active biological macromolecules and/or cell membrane constituents plays a key role in successfully transporting the therapeutic molecules into the cells. The lipopeptide of the present invention with CGKRK peptide head-group has certain common structural and functional groups. As such, the cationic amphiphiles is represented by the following formula A:

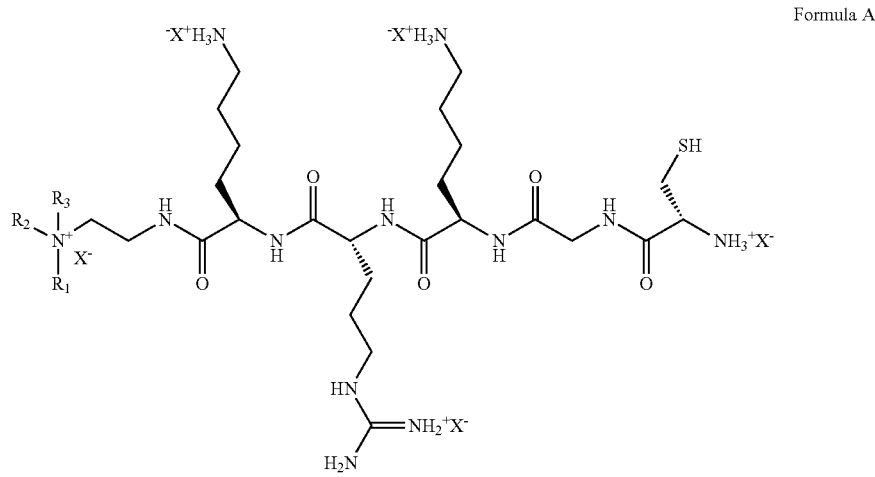

Formula A wherein,
the sequence of the peptide is CGKRK;
$R_1$ and $R_2$ are each independently selected from hydrogen or a lipophilic moiety containing eight to twenty four carbon atom selected from the group consisting of alkyl, mono-, di- and tri-unsaturated alkenyl, provided both $R_1$ and $R_2$ are not hydrogen;
$R_3$ is selected from a group consisting of hydrogen, $C_1$-$C_5$ alkyl, hydroxyl, and $C_1$-$C_5$ amino-alkyl; and
X is either chlorine or bromine
The cationic lipopeptide having formula A is represented by cationic CGKRK-lipopeptide 1.

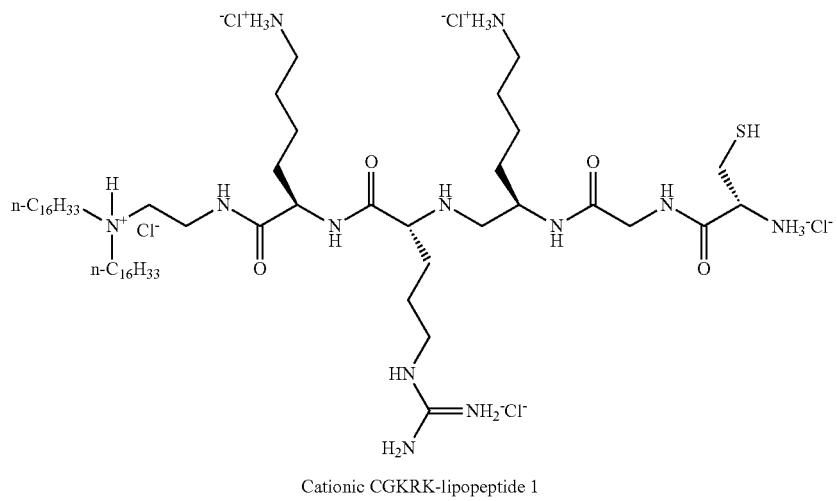

Cationic CGKRK-lipopeptide 1 wherein
$R_1$ and $R_2$=n-hexadecyl, $R_3$ is H and X is chlorine.

Synthesis of CGKRK-Lipopeptide 1

Synthetic strategies employed for preparing the cationic CGKRK-lipopeptides A are depicted schematically in Scheme 1 using CGKRK-lipopeptide 1 as an illustrative example. Scheme 1 is a schematic representation of the Fmoc strategy based solid phase peptide synthesis procedures used for the preparation of a representative cationic CGKRK-lipopeptide 1.

The Fmoc strategy based solid phase peptide synthesis route is used for preparing CGKRK-lipopeptide 1 (Scheme 1). H-Lys(Boc)-2-ClTrt resin-1 ($N^\epsilon$-Boc-Lysine pre-loaded 2-chloro trityl resin, Scheme 1) is first swelled in solvent and then coupled with Fmoc-Arg(Pbf)-OH using HATU and DIPEA to afford intermediate 2. The resin is then washed and the Fmoc group is removed with a solution of piperidine and DMF. Following the same Fmoc strategy, sequential couplings of Fmoc-Lys(Boc)-OH, Fmoc-Gly-OH, BOC-Cys(Trt)-OH using HATU and DIPEA affords the resin associated penta-peptide intermediate 3. The resin-bound intermediate 3 is taken out and treated with very dilute solutions of TFA to obtain protected penta-peptide intermediate 4. N,N-di-n-hexadecyl-N-2-aminoethylamine is coupled with protected penta peptide intermediate 4 to prepare the protected CGKRK-lipopeptide. To remove the protecting groups of amino acids the intermediate is treated with TFA-Thioanisole-EDT-TIS. The de-protected lipopeptide is purified using $Et_2O$ precipitation method. The precipitate upon chloride ion exchange chromatography over Amberlyst IRA-400 resin followed by purification with reversed phase HPLC affords the pure target CGKRK-lipopeptide 1 as a white, fluffy solid. The $^1H$ NMR spectra of the pure CGKRK-lipopeptideis thus taken in $CD_3OD/CDCl_3$ (3/1, v/v) mixed solvent. The final CGKRK-lipopeptide is characterized by the molecular ion peak in ESIMS and purity was confirmed by reversed phase analytical HPLC using two different mobile phases.

Scheme 1: Synthesis of CGKRK-lipopeptide 1
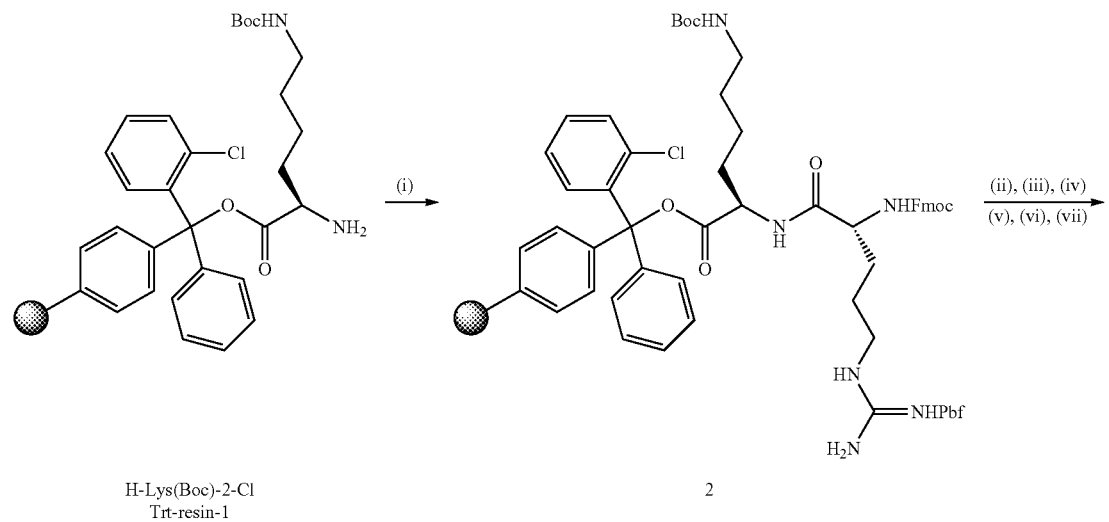
H-Lys(Boc)-2-Cl Trt-resin-1
2
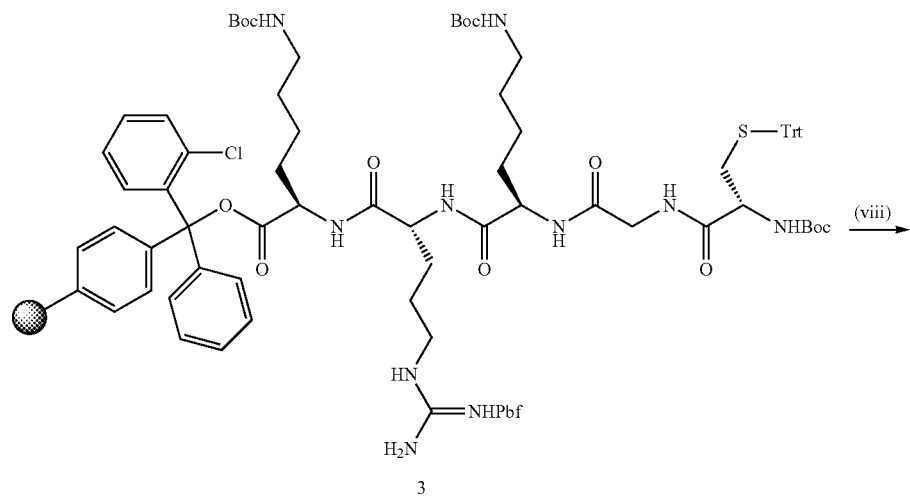
3
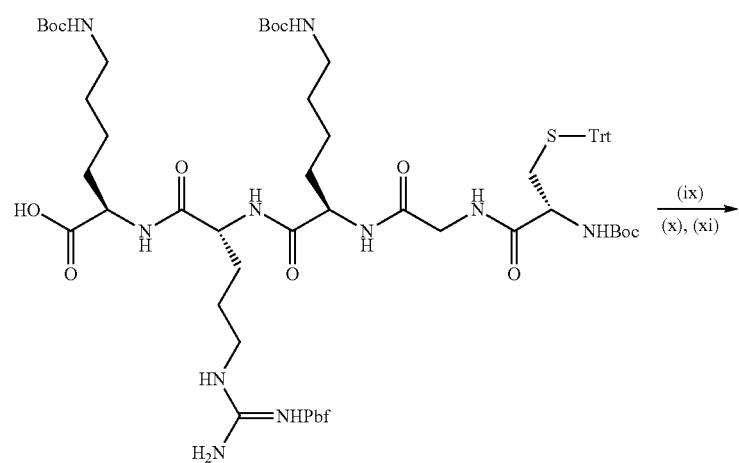
4

-continued

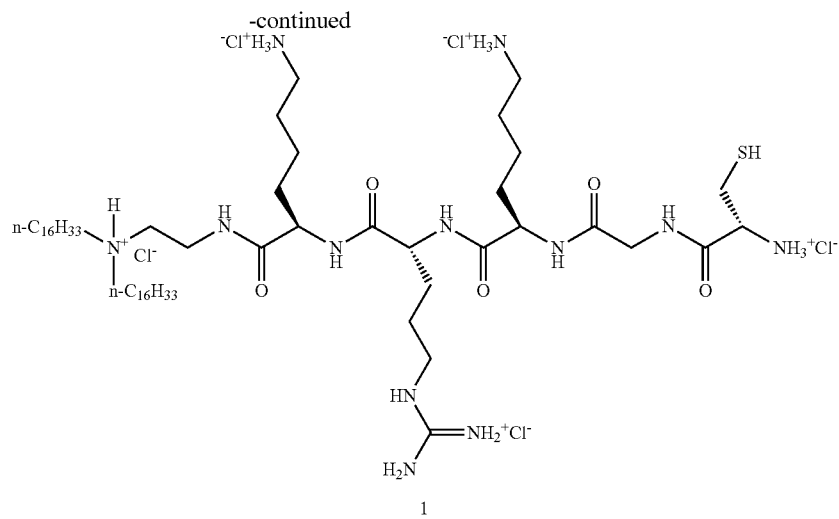

1

Formulations

The present invention provides a novel formulation comprising optimal amount of cationic lipopeptide with integrin targeting CGKRK head-groups, biological macromolecules and at least one co-lipid. One or more additional pharmaceutically acceptable substances can be included in the formulation of the present invention to stabilize the formulation for storage or to facilitate successful intracellular delivery of the biologically active molecules. Co-lipid of the present invention is useful for mixing with the cationic lipopeptide. Cholesterol is an excellent co-lipid for use in combination with the CGKRK-lipopeptide of the present invention to facilitate successful delivery of biologically active molecules in general, and WP1066 and stat3 siRNA in particular, to both endothelial cell and tumor cells. A preferred molar ratio of the cationic CGKRK-lipopeptide, di-cationic amphiphile and cholesterol in the formulation is 0.25:1:0.5. As such, it is within the art to vary the mole ratio of the CGKRK-lipopeptide, di-cationic amphiphiles and cholesterol to a considerably wide extent without compromising the therapeutic benefits of the present formulation. Typically, liposomes were prepared by dissolving the cationic CGKRK-lipopeptide and the co-lipids (Cholesterol and a non-targeting di-cationic amphiphile) in the appropriate mole ratio in a mixture of methanol and chloroform in a glass vial. The solvent was removed with a thin flow of moisture free nitrogen gas and the dried lipid film was then kept under high vacuum for 8 hrs. The dried lipid film was hydrated in sterile deionized water in a total volume of 1 mL at cationic lipid concentration of 1 mM for a minimum of 12 hrs. Liposomes were then vortexed for 1-2 minutes to remove any adhering lipid film and sonicated in a bath sonicator (ULTRAsonik 28X) for 2-3 min at room temperature to produce multilamellar vesicles (MLV). These MLVs were then sonicated with a Ti-probe (using a Branson 450 sonifier at 100% duty cycle and 25 W output power) for 1-2 minutes to produce small unilamellar vesicles (SUVs) as indicated by the formation of a clear translucent solution.

Integrin Specific Uptake of FITC-siRNA Encapsulated in Liposomes of CGKRK-Lipopeptide by Endothalial Cells (HUVEC)

To demonstrate the endothelial cell binding properties of the liposomes of CGKRK-lipopeptide of the present invention, a 3 hrs cellular uptake experiment in HUVEC cells was performed by encapsulating FITC-siRNA in the formulation of CGKRK-lipopeptide of the present invention. Epifluorescence micrographs of the treated endothelial cells convincingly demonstrated endothelial cell binding efficiency of the liposomes (FIG. 1). Importantly, the cellular uptake efficiencies were found to be considerably inhibited when HUVEC cells were pre-incubated with any one of the monoclonal antibodies against $\alpha 5\beta 1$, $\alpha v\beta 3$ and $\alpha v\beta 5$ integrins (FIG. 1). Thus, the findings summarized in FIG. 1 confirm that formulation of CGKRK-lipopeptide of the present invention are capable of effectively delivering small non-coding RNAs to endothelial cells via all three $\alpha 5\beta 1$, $\alpha v\beta 3$ and $\alpha v\beta 5$ integrin receptors.

WP1066, a Potent Commercially Available Inhibitor of stat3 Phosphorylation and stat3 siRNA Co-Encapsulated in Liposomes of CGKRK-Lipopeptide Show Synergic Effect in Inducing Apoptosis in Tumor Cells (B16F10)

To evaluate the in-vitro efficiencies of liposomally encapsulated WP1066 and stat3siRNA in inducing apoptosis in tumor cells (B16F10), conventional Annexin V/Propidium iodide (PI) binding based flow cytometric apoptosis assay protocols was used. When WP1066 and stat3siRNA were both co-encapsulated in liposomes of CGKRK-lipopeptides of the present invention, the degree of apoptosis induced in tumor cells were observed to be remarkably higher than that observed in tumor cells treated with stat3siRNA or WP1066 individually encapsulated (i.e. not in combination) in liposomes of CGKRK-lipopeptides of the present invention (FIG. 2). Such findings in flow cytometric apoptosis assay are fully consistent with synergic effects of WP1066 and stat3 siRNA in inducing apoptosis in tumor (B16F10) cells.

Figure 3A:
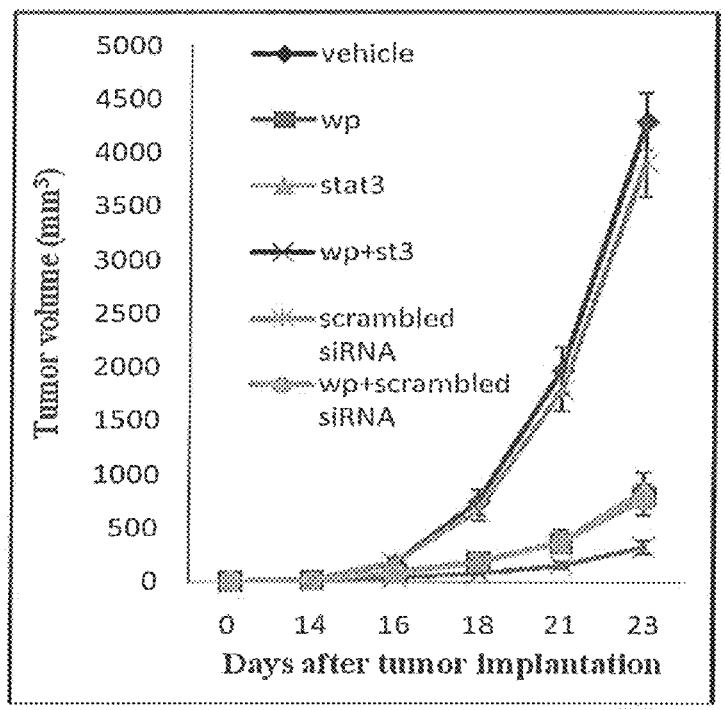
FIGS. 3A-3C show that WP1066 and stat3 siRNA co-encapsulated in liposomes of CGKRK-lipopeptide 1 show synergic effect in inhibiting B16F10 melanoma tumor growth through induction of apoptosis in tumor endothelial cells.
Figure 3B:
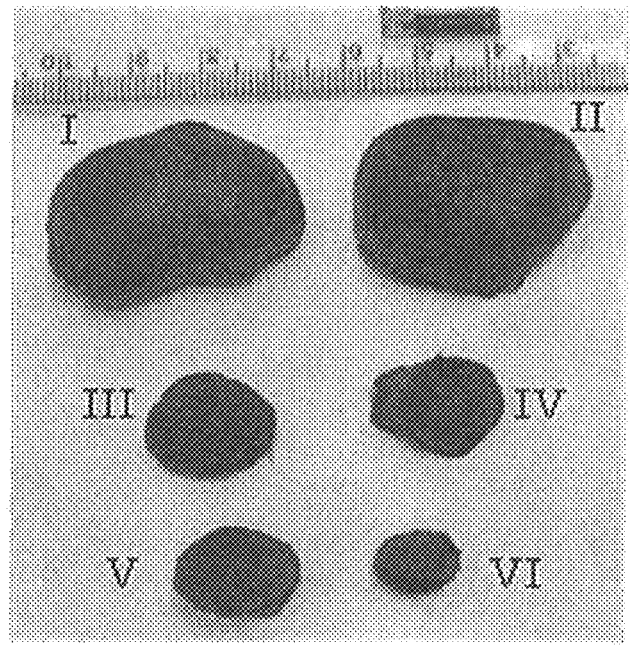
Figure 3C:
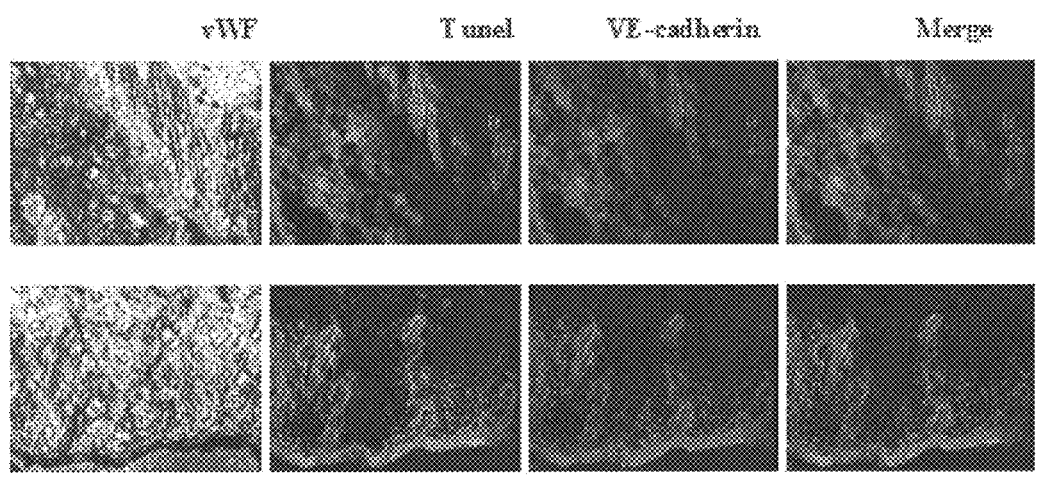

WP1066 & stat3siRNA Co-Encapsulated in Liposomes of CGKRK-Lipopeptide of the Present Invention Show Synergic Effect to Inhibit B16F10 Melanoma Tumor Growth by Inducing Apoptosis of Tumor Endothelial Cells To evaluate the synergic effect of WP1066 and stat3 siRNA for inhibition of tumor growth in a syngeneic mouse model, liposomally bound WP1066 and stat3 siRNA were intravenously administered in C57BL/6J mice bearing melanoma tumors. Most significant tumor growth inhibition was observed when tumor bearing mice (n-5) were i.v. injected with WP1066 and stat3 siRNA co-encapsulated in liposomes of CGKRK-lipopeptide of the present invention (FIG. 3A-B). Tumor vasculature targeting liposomes of CGKRK-lipopeptide encapsulating only WP 1066 and only stat3 siRNA were found to be significantly (by 2-3 folds) less efficient in inhibiting melanoma tumor growth in syngeneic mice when compared to degree of tumor growth inhibition observed with intravenously administered WP1066 and stat3siRNA both co-encapsulated in liposomes of CGKRK-lipopeptide (FIG. 3A-B). Mice intravenously administered with vehicle alone (in 5% aqueous glucose solution) developed large tumor on day 22 (FIGS. 3A-B) and were sacrificed. Since liposomes of CGKRK-lipopeptide of the present invention is efficient to target endothelial cells (FIG. 1), with a view to address whether the tumor growth inhibition properties of the liposomal formulation of WP1066 and stat3 siRNA of the present invention result from apoptosis of tumor endothelial cells, mice treated with WP1066 and stat3 siRNA co-encapsulated in liposomes of CGKRK-lipopeptide of the present invention were sacrificed. The tumors were excised, cryosectioned, fixed and the fixed frozen sections were treated with TUNEL assay kit for marking the apoptotic cells. Subsequently, same tumor cryosections were immunounostained with both vWF and vascular endothelial (VE)-cadherin-specific antibodies to identify tumor vasculatures. The TUNEL-positive cells (i.e. cells undergoing apoptosis) were found to be co-localized with tumor endothelial cells across the entire cryosections (FIG. 3C). Thus, the findings in the immunohistochemical staining assays summarized in FIG. 3 are consistent with the notion that the remarkable tumor growth inhibition observed in mice treated with CGKRK-lipopeptide formulation of WP1066 and stat3 siRNA of the present invention is mediated via apoptosis of the tumor endothelial cells. Increased number of TUNEL positive cells in tumor sections from mice treated with WP 1066 and stat3 siRNA co-encapsulated in liposomes of CGKRK-lipopeptide of the present invention shows effectiveness of using combination of potent chemotherapeutics in anti-angiogenic cancer therapy.

Figure 4A:
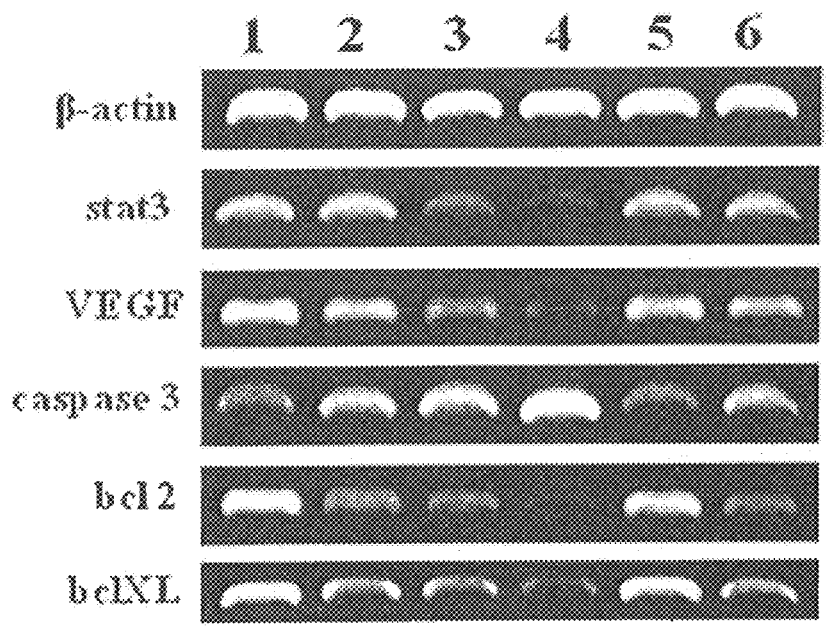
FIGS. 4A-4C depict synergistic effects of WP1066 and stat3siRNA co-encapsulated in liposomes of CGKRK-lipopeptide toward inhibiting stat3-phosphorylation both in vitro and in vivo.
Figure 4B:
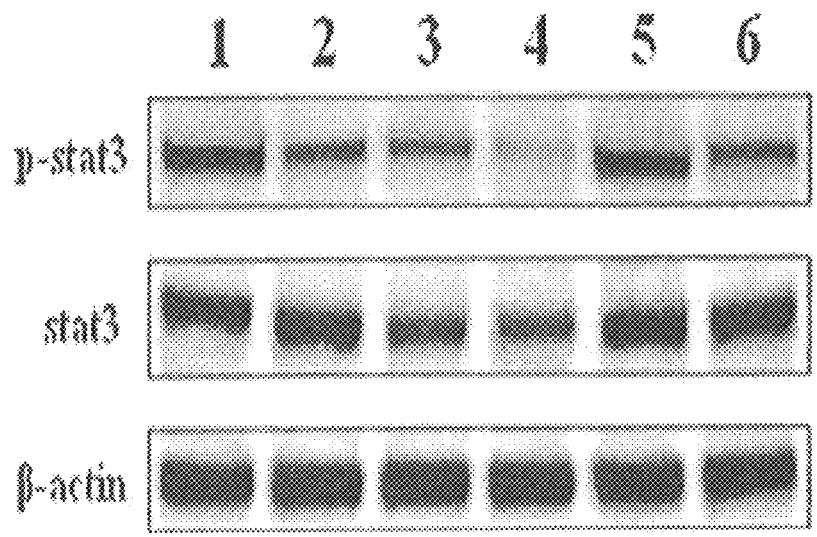
Figure 4G:
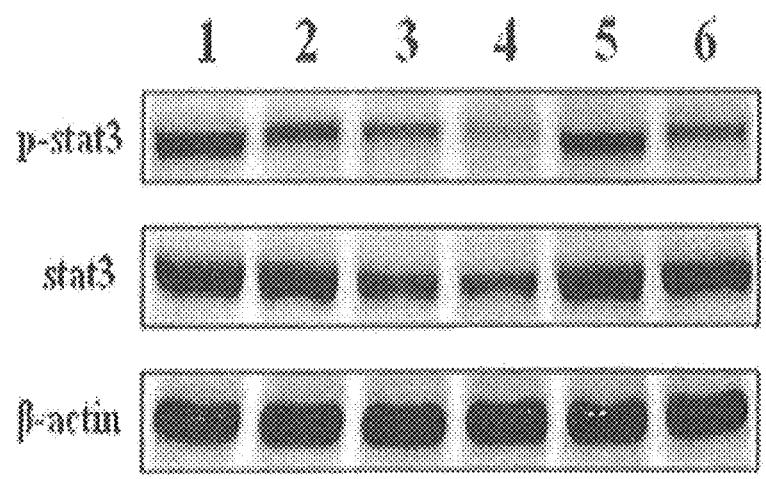

Inhibition of stat3-Phosphorylation by Liposomal Formulation of stat3siRNA and WP1066 of the Present Invention To examine the possible inhibition of stat3-phosphorylation in B16F10 cells treated with liposomal formulation of stat3 siRNA and WP 1066 of the present invention, the expression of some of the representative genes involved in stat3 signaling pathways (VEGF, stat3, Bcl2, BclX$_L$, caspase3) was measured at mRNA levels in treated cells using RT-PCR. Importantly, the decrease in expression of cell proliferating VEGF, stat3, Bcl2, BclX$_L$ genes and increase in expression of apoptosis inducing caspase3 gene were observed in B16F10 cells treated with liposomally encapsulated stat3 siRNA compared to untreated cells (FIG. 4A). To analyze the expression of some representative proteins, the amount of stat3 and p-stat3 at protein levels was measured in B16F10 cells treated with liposomal formulation of stat3siRNA and WP1066 of the present invention using Western Blot experiments. Level of p-stat3 protein was found to be significantly reduced in B16F10 cells treated with liposomal formulation of stat3siRNA and/or WP1066 compared to untreated cells (FIG. 4B). Importantly, it was evident that treatment with liposomally co-encapsulated combination of chemotherapeutics was more potent to inhibit stat3 signaling pathways at both mRNA and protein levels when compared to their levels in cells treated with liposomal formulation of single therapeutic agent (FIG. 4). Moreover, liposomally encapsulated scrambled siRNA shows no effect in stat3 signalling pathway (FIG. 4). Decrease in p-stat3 protein level was also observed in B16F10 cells isolated from tumors treated with stat3-siRNA and/or WP1066 co-encapsulated in liposomes of CGKRK-lipopeptide of the present invention when compared to its level in tumor cells from untreated mice (FIG. 4C).

Simultaneous Application of Targeted Chemotherapy and Cancer Immunotherapy to Regress Established Melanoma Tumor in Syngeneic Mouse Tumor Model To examine the efficiency of combined therapeutic modality (i.e. simultaneous application of targeted chemotherapy and cancer immunotherapy), mice were subcutaneously immunized with melanoma tumor antigen encoded DNA vaccine (p-CMV-MART1 plasmid DNA) electrostatically complexed with direct in-vivo DC-targeting liposomes of lysinylated cationic amphiphiles with guanidine and mannose-mimicking shikimoyl head-groups (using 200 μL 5% glucose solution containg 15 μg DNA, 4:1 lipid:DNA ratio for each mice) on day 15 and 17 after tumor implantation. Tumor growth inhibition studies (as provide in FIG. 5A) suggest that only genetic immunization (i.e. without using chemotherapeutic in combination with DNA vaccine) is not capable of regressing established tumor growth. Importantly, targeted intravenous administration of stat3 siRNA (2 μg/mice) and WP1066 (10 mg/kg B.W of mice) co-encapsulated in liposomes of CGKRK-lipopeptide of the present invention on day 14, 16, 19, 21 and 24 post tumor inoculation in combination with subcutaneous genetic immunization with lipoplexes of the melanoma antigen encoded DNA vaccine (p-CMV-MART1) in complexation with direct in-vivo mouse DCs targeting liposomes was capable of providing essentially complete regression of even established tumor (FIG. 5A) thereby demonstrating the remarkable therapeutic potential of such combination therapy in combating cancer.

In summary, the ingredients of liposomal formulation of the present invention for targeted chemotherapy include integrin receptor selective novel lipopeptide comprising a both tumor and tumor vasculature targeting CGKRK-pentapeptide head-group and a long aliphatic hydrocarbon chain, at least one co-lipid, a potent cytotoxic drug and a cell proliferation inhibiting small non-coding RNA. The liposome of CGKRK-lipopeptide of the present invention can target genes/drugs to endothelial cells (HUVEC) as well as tumor cells (B16F10) via any of the three widely used integrin receptors namely, αvβ3, αvβ5 & α5β1 integrin receptors. The findings disclosed herein demonstrate that intravenous administration of liposomal formulation of the CGKRK-lipopeptide containing encapsulated potent cytotoxic drug such as WP 1066 (a commercially available inhibitor of stat3 phosphorylation) and stat3-siRNA (a commercially available cell proliferation inhibiting small non-coding RNA) leads to significant tumor growth inhibition in a syngenic mouse tumor model by inducing apoptosis in tumor endothelial cells. Importantly, when mice receiving the liposomal formulation of the present invention for targeted chemotherapy were simultaneously immunized with an electrostatic complexe of direct in-vivo dendritic cell (DC) targeting cationic liposomes & DNA vaccine encoding melanoma tumor associated antigens (genetic immunization), even established melanoma tumor completely regressed in 4 out of 5 treated mice. The combined therapeutic modality disclosed herein holds the potential of becoming a platform technology for combating various dreadful cancers.

EXAMPLES

The following examples are given by of illustrating the present invention and should not be construed to limit the scope of the invention.

Example 1

Synthesis of CGKRK-Lipopeptide (A)

Fmoc strategy based solid phase peptide synthesis procedure was employed for preparing the cationic lipopeptide with integrin targeting CGKRK head group as depicted schematically in Scheme 1. 100 mg of H-Lys(Boc)-2-ClTrt resin-1 ($N^\epsilon$-Boc-Lysine pre-loaded 2-chloro trityl resin, 0.72-0.77 mmol/g loading) was first swelled in 10 mL DMF for 4 hrs and then coupled with Fmoc-Arg(Pbf)-OH (2 equiv) using HATU) (2 equiv) and DIPEA (4 equiv) in DMF at room temperature for 1.5 hrs to afford intermediate 2. The resin was then washed with DMF and the Fmoc group was removed with a solution of piperidine:DMF (1:4, v/v, 10 mL, 4 min, 2 times) at room temperature. Following the same Fmoc strategy, sequential couplings of Fmoc-Lys(Boc)-OH, Fmoc-Gly-OH, BOC-Cys(Trt)-OH (2 equiv each) using HATU (2 equiv) and DIPEA (4 equiv) in DMF at room temperature for 1.5 hrs for each amino acid afforded the resin associated penta peptide intermediate 3. The resin-bound penta peptide intermediate 3 was taken out of the reaction vessel with excess DCM, washed thoroughly with DCM (5×10 mL) and dried well. The resulting dried resin bound intermediate was treated with TFA:DCM (0.5%, v/v, 70 mL) for 2 h at 0° C. to obtain a protected penta peptide intermediate 4 (0.058 g, 58%). N,N-di-n-hexadecyl-N-2-aminoethylamine (0.023 g, 0.046 mmol) was then dissolved in dry DCM (3 mL) and the solution was added to an ice cold reaction mixture (which has been under stirring conditions for 30 min) containing EDCI (8.2 mg, 0.042 mmol), HOBT (6.4 mg, 0.042 mmol) and the protected penta peptide intermediate 4 (0.058 g, 0.042 mmol) in dry DCM (5 mL). The resulting solution was left under stirring conditions at room temperature for 12 hrs. The solvent was then evaporated in the rotary evaporator at 30° C. and the residue was dried completely under high vacuum. The dried intermediate was treated with TFA-Thioanisole-EDT-TIS (90:5:3:2 v/v, 2 mL) for 3 hrs at 0° C. and washed with TFA:DCM (1:9, v/v, 8 mL). The acid washings were concentrated to about 1 mL and $Et_2O$ was added until a white precipitate separated. The precipitate upon chloride ion exchange chromatography over Amberlyst IRA-400 resin followed by purification with reversed phase HPLC afforded the pure CGKRK-lipopeptide (A) as a white, fluffy solid (25 mg, 55% based on penta peptide intermediate 4). The purified CGKRK-lipopeptide was found to be essentially insoluble in chloroform and could be dissolved in 3:1 (v/v) methanol:chloroform. The $^1$H NMR spectra of the pure CGKRK-lipopeptide was thus taken in $CD_3OD/CDCl_3$ (3/1, v/v) mixed solvent. The final CGKRK-lipopeptide 1 was characterized by the molecular ion peak in ESIMS and purity was confirmed by reversed phase analytical HPLC using two different mobile phases. ESIMS: m/z=1082 $[M+1]^+$ for $C_{57}H_{116}N_{12}O_5S$.

$^1$H NMR (200 MHz, $CDCl_3+CD_3OD$): δ/ppm=0.9 [t, 6H, $C\underline{H}_3$—$(CH_2)_{15}$—]; 1.1-1.5 [bs, 56H, —$(C\underline{H}_2)_{14}$—; m, 6H, Lys $C^\beta\underline{H}_2$+Arg $C^\beta\underline{H}_2$]; 1.5-2 [m, 8H, Lys $C^\gamma\underline{H}_2$+Lys $C^\delta\underline{H}_2$; m, 2H, Arg $C^\gamma\underline{H}_2$; m]; 2.5-3.3 [m, 4H, —N(—C$\underline{H}_2$—$CH_2$—$)_2$; m, 2H, —N—$C\underline{H}_2$—$CH_2$—NH—CO; m, 4H, Lys $C^\omega\underline{H}_2$; m, 2H, Arg $C^\delta\underline{H}_2$; m, 2H, Cys $C^\beta\underline{H}_2$]; 3.5-3.8 [m, 2H, —N—$CH_2$—$C\underline{H}_2$—NH—CO—; m, 2H, Lys $C^\alpha\underline{H}$; m, 1H Cys $C^\alpha\underline{H}$; m, 1H, Arg $C^\alpha\underline{H}$]; 4.4-4.5 [m, 2H, Gly $C^\alpha\underline{H}_2$].

Example 2

Evaluation of Integrin Receptor Specific siRNA Delivery Efficacy of CGKRK-Lipopeptide in Endothalial Cells (HUVEC)

Preparation of Liposomally Encapsulated FITC-siRNA

Lipopeptide and co-lipids (Cholesterol and di-cationic amphiphile) taken at 0.25:1:0.5 molar ratio of CGKRK-lipopeptide 1:di-cationic amphiphiles:cholesterol were dissolved in chloroformmethanol mixture (1:1, v/v). The mixture was then evaporated under a thin stream of nitrogen gas, vacuum dried for 8 h and hydrated in deionised water containing FITC-siRNA (total lipid: FITC-siRNA in the ratio of 25:1 w/w) for overnight to obtain a hydrated lipid film with a final lipid concentration of 1 mM for in-vitro experiments or 5 mM for in-vivo experiments. The hydrated lipid film was first vortexed for 30 seconds, bath sonicated for 1 min and then frozen and thawed 15-20 times at −78° C. Unentrapped FITC-siRNA was separated by using amicon ultra centrifugation (30 kD). Concentration of liposomally entrapped FITC-siRNA was determined by fluorescence intensity measurements using a standard graph constructed from pure FITC-siRNA samples.

Integrin Receptor Selectivity Studies.

HUVEC cells were seeded at a density of ~10,000 cells per well in a 96-well plate for 18-24 h before treatment. The cells were separately pre-incubated with 50 μL monoclonal antibodies against the αvβ3, αvβ5 and α5β1 integrins (at a dilution of 1:25 in EBM2 containing 10% FBS (v/v) for 45 min at room temperature. After 45 min, media were taken out and a fresh lot of 50 μL monoclonal antibody solutions (at a dilution of 1:25 in 10% complete medium) was added to each well. 50 μL of media containing FITC-siRNA encapsulated in liposomes of CGKRK-lipopeptide 1 was added to each well. After 3 h incubation at 37° C., the cells were washed with phosphate buffer saline and the alive HUVEC cells were viewed with an epifluorescence microscope. Representative findings in the above mentioned epifluorescence microscopy experiments is provided in FIG. 1 wherein Epifluorescence microscopic images of control cells (A-C; cells without antibody pretreatment) and cells pre-treated with monoclonal antibody against α5β1 integrin receptors (D-F), αvβ3 integrin receptors (G-I) and αvβ5 integrin receptors (J-L) were taken post 3 h of liposome addition. Left panel (A, D, G, J) represents the bright field images of HUVEC cells; middle panel (B, E, H, K) represents the uptake of FITC labeled siRNA (green); right panel (C, F, I, L) represents merge pictures of left and middle panel that indicates uptake of FITC labeled siRNA in HUVEC. Epifluorescence micrographs of the treated endothelial cells convincingly demonstrated endothelial cell binding efficiency of the liposomes. Uptake of liposomally encapsulated FITC labeled siRNA in antibody pre-treated cells (D-K) is less than antibody untreated cells (A-C), indicating cellular uptake of FITC labeled siRNA via all three α5β1, αvβ3 and αvβ5 integrin receptors. Thus, the findings summarized in FIG. 1 confirm that CGKRK-lipopeptide 1 are capable of effectively delivering small non-coding RNAs to endothelial cells via all three α5β1, αvβ3 and αvβ5 integrin receptors.

Example 3

Preparation of Liposomal Formulation of CGKRK-Lipopeptide 1 and Chemotherapeutic Agents The liposomal formulation of CGKRK-lipopeptide 1 was prepared using cholesterol and the di-cationic amphiphiles (n-$C_{16}H_{33}$)$_2$N$^+$(CH$_3$)CH$_2$CH$_2$N$^+$(CH$_3$)$_3$2Cl$^-$ as co-lipids wherein the mole ratio of the lipopeptide:dicationic amphiphile:cholesterol is 0.25:1:0.5. To prepare liposomal formulation containing WP 1066, a stock solution of WP 1066 was prepared by dissolving the same in chloroform (5 mg/mL). The final ratio of total lipid:WP1066 by weight used for preparing the liposomal formulation containing only WP1066 was 10:1 for both in-vitro and in-vivo experiments. Similarly, the final ratio of total lipid:WP1066 by weight used for preparing the liposomal formulation containing both WP1066 and STAT3siRNA was also 10:1 for both in-vitro and in-vivo experiments. The appropriate lipid mixtures were dissolved in a mixture of chloroform and methanol (3:1, v/v) in a glass vial and the solvent was removed with a thin flow of moisture free nitrogen gas. The dried lipid film was then kept under high vacuum for 8 h and hydrated for overnight in autoclaved water to prepare the liposomal formulation containing only WP1066 or in a nuclease free water containing siRNA-protamine complex (total lipid:siRNA (w/w, 25:1); siRNA:protamine (w/w, 1:10)) to prepare liposomal formulation containing either only siRNA or both siRNA and WP1066. The hydrated lipid film was first vortexed for 1-2 minutes at room temperature to produce multilamellar vesicles (MLVs). For liposomal formulation containing only WP1066, MLVs were then sonicated in an ice bath until clarity using a Branson 450 sonifier at 100% duty cycle and 25 W output power to produce small unilamellar vesicles (SUVs). For liposomal formulation containing only siRNA, MLVs were bath-sonicated for 1 min to produce small unilamellar vesicles (SUVs) and then frozen & thawed 16-20 times at −78° C. to achieve equilibrium transmembrane solute distributions. Unentrapped siRNA was eluted using amicon ultra centrifugal filter units (10 kD) and the liposomes were finally concentrated using amicon ultra to make the final concentration of the co-lipids to 1 mM for in-vitro experiments or 5 mM for in-vivo experiments.

Example 4

WP1066 (a Potent Inhibitor of stat3-Phosphorylation) and stat3siRNA Show Synergic Effect in Inducing Apoptosis of Tumor Cells (B16F10)

Apoptosis Analysis by Flow Cytometry

B16F10 cells were seeded at a density of ~3×10$^5$ cells/well in a 6 well plate for 18-24 h before treatment. Cells were treated for 4 hrs with: (a) WP1066 (2 μM) solubilized in liposomes of CGKRK-lipopeptide 1 (liposomal formulation of WP1066); (b) stat3-siRNA (20 nM) encapsulated in liposomes of CGKRK-lipopeptide 1 (liposomal formulation of stat3-siRNA); and (e) both WP1066 (2 μM) and stat3 siRNA (20 nM) co-encapsulated in liposomes of CGKRK-lipopeptide 1 (liposomal formulation of WP1066 and stat3-siRNA) in a total 1.5 mL of complete media (DMEM containing 10% FBS, v/v)). After 4 h of incubation at 37° C., the media was completely replaced with 2 mL fresh complete medium and incubated for 24 h. Cells were then trypsinized, washed with PBS, centrifuged and the pellet was resuspended in 200 μL binding buffer containing annexin-V FITC (0.25 μg) and propidium iodie (PI) (1.0 μg). The mixture was then incubated for 15 min in dark and analyzed by flow cytometer (BD FACS Canto II).

The results obtained in the experiment described above is summarized in FIG. 2 wherein cells were treated with: WP1066 2 μM solubilized in liposome of CGKRK-lipopeptide 1 (B), stat3-siRNA (20 nM) encapsulated in liposome of CGKRK-lipopeptide 1 (C) and both WP1066 (2 μM) & stat3-siRNA (20 nM) co-encapsulated in liposome of CGKRK-lipopeptide I (D). Both untreated (A) and treated cells (B-D) were stained with FITC-Annexin V and propidium iodie (PI) for flow cytometric analysis. The horizontal and vertical axes represent cells labeled with FITC-Annexin V and PI, respectively, in the dot plot. Dots (percentage) in the lower left quadrant represent live cells (negative for both Annexin V and PI). Dots (percentage) in the lower right quadrant represent early apoptotic cells (positive for Annexin V and negative for PI). Dots (percentage) in the upper left quadrant represent necrotic cells (negative for Annexin V and positive for PI). Dots (percentage) in the upper right quadrant represent late apoptotic cells (positive for both Annexin V and PI).

When both WP1066 and stat3siRNA were co-encapsulated in liposomes of CGKRK-lipopeptide 1, the degree of apoptosis induced in tumor cells were observed to be remarkably higher than that observed in tumor cells treated with stat3 siRNA or WP1066 individually encapsulated (i.e. not in combination) in liposome of CGKRK-lipopeptide 1. Such findings in flow cytometric apoptosis assay are fully consistent with synergic effects of WP1066 and stat3 siRNA in inducing apoptosis in tumor (B16F10) cells.

Example 5

WP1066 and stat3 siRNA when Co-Encapsulated in Liposome of CGKRK-Lipopeptide 1 Show Synergic Effect to Inhibit B16F10 Melanoma Tumor Growth by Inducing Apoptosis of Tumor Endothelial Cells Tumor Growth Inhibition Study B16F10 melanoma cells were harvested from T25 culture flasks using 1 mL cell dissociation solution (Sigma, USA), washed with PBS (2×200 μL) and resuspended in HBSS. Approximately 1.5×10$^5$ B16F10 melanoma cells in 100 μL, HBSS were s.c. injected in the right flank of 6-8 weeks old female C57BL/6J mice (each weighing 20-22 g) on day 0. On day 14, mice injected with B16F10 cells were randomly sorted into six groups and each group (n=5) was administered intravenously with the following different formulations: Group I was injected with stat3-siRNA (2 μg/mice) and WP1066 (10 mg/kg B.W of mice) both co-encapsulated in liposome of CGKRK-lipopeptide 1; Group II was injected with WP1066 (10 mg/kg B.W of mice) alone solubilized in liposomes of CGKRK-lipopeptide 1; Group III was injected with stat3 siRNA (2 μg/mice) alone encapsulated in liposome of CGKRK-lipopeptide 1; Group IV was injected with scrambled siRNA (2 µg/mice) and WP1066 (10 mg/kg B.W of mice) both co-encapsulated in liposome of CGKRK-lipopeptide 1; Group V was injected with scrambled siRNA (2 µg/mice) alone encapsulated in liposome of CGKRK-lipopeptide 1. Each of these intravenous treatment was performed on day 14, 16, 19, 21 and 23 post tumor inoculation. The sixth group (n=5) was intravenously injected with vehicle (5% aqueous glucose) alone. Tumor volumes ($V=\frac{1}{2} \cdot ab^2$ where, a=maximum length of the tumor and b=minimum length of the tumor measured perpendicular to each other) were measured with a slide calipers for up to 23 d post tumor inoculation.

Study of Apoptosis of Tumor Vasculatures (TUNEL Assay)

Tumors were excised 24 h post last injection, frozen in a cryostat at −30° C. for 2 h, cryosectioned and ten micrometer frozen cryosections were fixed in 4% methanol free formaldehyde solution for 30 min. Fixed tumor sections were washed twice with PBS for 5 min and immunostained with anti-vWF (marker of tumor endothelial cells, bright field) staining kit. The same tumor cryosections were then immunostained with TUNEL assay kit (markers for apoptotic cells, green) followed by immunostained with anti-VE-cadherin antibodies (another tumor neovasculature marker, red). The $4^{th}$ panels show superimposed images. All the images were taken at 10× magnification.

The results obtained for the above experiment is provided in FIG. 3. FIG. 3A shows that tumor vasculature targeting liposomes of CGKRK-lipopeptide 1 encapsulating only WP1066 and only stat3 siRNA were found to be significantly (by 2-3 folds) less efficient in inhibiting melanoma tumor growth in syngeneic mice when compared to degree of tumor growth inhibition observed with intravenously administered WP 1066 & stat3siRNA both co-encapsulated in liposomes of CGKRK-lipopeptide 1.

FIG. 3B provides the image of representative samples of B16F10 tumors excised on day 24 after tumor inoculation.

It was observed from FIG. 3C that the TUNEL-positive cells (i.e. cells undergoing apoptosis) were found to be co-localized with tumor endothelial cells across the entire cryosections.

Thus, the findings in the immunohistochemical staining assays summarized in FIG. 3 are consistent with the notion that the remarkable tumor growth inhibition observed in mice treated with CGKRK-lipopeptide 1 formulation of WP1066 and stat3 siRNA via apoptosis of the tumor endothelial cells. Increased number of TUNEL positive cells in tumor sections from mice treated with WP 1066 and stat3 siRNA co-encapsulated in liposomes of CGKRK-lipopeptide 1 shows effectiveness of using combination of potent chemotherapeutics in anti-angiogenic cancer therapy.

Example 6

Inhibition of stat3 Signaling Pathway by Liposomal Formulation of stat3 siRNA and WP1066

RT-PCR (Reverse Transcriptase-PCR) Analysis.

B16F10 cells were seeded at a density of ~$1.0 \times 10^6$ cells in a T25 flask 18-24 h before treatment. Cells were treated with: stat3 siRNA (20 nM) encapsulated in liposome of CGKRK-lipopeptide 1, WP1066 (2 µM) solubilized in liposome of CGKRK-lipopeptide 1, both stat3 siRNA (20 nM) & WP1066 (2 µM) co-encapsulated with liposome of CGKRK-lipopeptide 1, scrambled siRNA (20 nM) encapsulated in liposome of CGKRK-lipopeptide 1, both scrambled siRNA (20 nM) & WP1066 (2 µM) co-encapsulated in liposome of CGKRK-lipopeptide 1 in 3 mL final volume of complete medium (DMEM containing 10% FBS, v/v) for 4 h. After 4 h incubation, the medium was completely removed and 3.0 mL fresh complete medium was added. After 24 h of treatment, total RNA were extracted from treated and untreated cells using TRIzol® reagent (Invitrogen). First-strand cDNAs were synthesized from the corresponding mRNAs by reverse transcription reaction according to the Manufacturer's instructions (Reverse Transcription System, Promega, USA). cDNAs were amplified using PCR master mix (Promega, USA) and the following forward and reverse primers (Biotek Desk, USA):

| mRNA type | Primer type | Primer sequence |
|---|---|---|
| Mouse STAT3 | Forward | 5'ACCCAACAGCCGCCGTAG3' |
| | Reverse | 5'CAGACTGGTTGTTTCCATTCAGAT3' |

The amplified sequences were finally resolved in 2% agarose gel electrophoresis and visualized using 0.1% ethidium bromide under UV light.

Western Blot Analysis

B16F10 cells were seeded at a density of ~$1 \times 10^6$ cells in T-25 flasks 18-24 h before treatment. Cells were treated with: stat3siRNA (20 nM) encapsulated in liposome of CGKRK-lipopeptide 1, WP1066 (2 µM) solubilized in liposome of CGKRK-lipopeptide 1, both stat3 siRNA (20 nM) & WP1066 (2 µM) co-encapsulated in liposome of CGKRK-lipopeptide 1, scrambled siRNA (20 nM) encapsulated in liposomes of CGKRK-lipopeptide 1, both scrambled siRNA (20 nM) and WP1066 (2 µM) co-encapsulated in liposome of CGKRK-lipopeptide 1 in 3 mL final volume of complete medium. After 4 hrs of incubation, the medium was completely removed and 3 mL fresh complete medium was added. After 24 h of treatment, cells were detached from the flask using a cell scrapper and the cell lysates were prepared by lysing the cells with lysis reagent (CCLR, Promega, USA) at 4° C. Total protein content of the cell lysate was quantified by BCA assay method and 80 µg of total protein was dissolved in SDS-PAGE sample buffer prior to separation by 7.5% SDS-PAGE. Proteins were transferred onto nitrocellulose membrane (Hybond-ECL, Amersham Biosciences, NJ) using wet blotting. Membranes were blocked for 2 h at room temperature with 5% non-fat milk in PBS containing 0.05% Tween-20 (PBS-T). Blot were then incubated with Rabbit Polyclonal PhosphoDetect Anti-phospho stat3, Rabbit Polyclonal Anti-stat3 and Rabbit Polyclonal Anti-β actin (as loading control) with primary antibody at 1:1000 dilution (in 10 mL 0.05% PBS-T) for overnight at 4° C. After washing with PBS-T (3×10 mL, 10 min), the membranes were incubated with goat anti-rabbit secondary antibody conjugated to alkaline phosphatase (in 10 mL 0.05% TBS-T at 1:2000 dilution) for 2 h. Protein bands were developed using BCIP/NBT chromogen solution (Calbiochem, USA).

Inhibition of stat3 Phosphorylation In Vivo

B16F10 melanoma cells were harvested from T25 culture flasks using 1 mL cell dissociation solution (Sigma, USA), washed with PBS (2×200 µL) and resuspended in HBSS. ~$1.5 \times 10^5$ B16F10 melanoma cells in 100 µL, HBSS were s.c. injected in the right flank of 6-8 weeks old female C57BL/6J mice (each weighing 20-22 g) on day 0. On day 12, mice injected with B16F10 cells were randomly sorted into six groups and each group (n=5) was administered intravenously with the following different formulations: Group I was injected with stat3 siRNA (2 µg/mice) and WP1066 (10 mg/kg B.W of mice) both co-encapsulated in liposome of CGKRK-lipopeptide 1; Group II was injected with WP1066 (10 mg/kg B.W of mice) alone solubilized in liposome of CGKRK-lipopeptide 1; Group III was injected with stat3 siRNA (2 µg/mice) alone encapsulated in liposome of CGKRK-lipopeptide 1; Group IV was injected with scrambled siRNA (2 µg/mice) and WP1066 (10 mg/kg B.W of mice) both co-encapsulated in liposome of CGKRK-lipopeptide 1; Group V was treated with scrambled siRNA (2 µg/mice) alone encapsulated in liposome of CGKRK-lipopeptide 1. Each of these intravenous treatment was performed on day 14, 16, 19, 21 and 23 post tumor inoculation. The sixth group (n=5) was intravenously injected with vehicle (5% aqueous glucose) alone. On day 24, mice were sacrificed, the tumor was excised and B16F10 cells were isolated from tumor. The cell lysates were prepared by lysing the cells with lysis reagent (CCLR, Promega, USA) at 4° C. and subjected to Western Blotting experiment.

Results obtained in the experiment is provided in FIG. 4.

To examine the possible inhibition of stat3-phosphorylation in B16F10 cells treated with liposomal formulation of stat3 siRNA and WP 1066, the expression of some of the representative genes involved in stat3 signaling pathways (VEGF, stat3, Bcl2, BclX$_L$, caspase3) was measured at mRNA levels in treated cells using RT-PCR. Importantly, the decrease in expression of cell proliferating VEGF, stat3, Bcl2, BclX$_L$ genes and increase in expression of apoptosis inducing caspase3 gene were observed in B16F10 cells treated with liposomally encapsulated stat3 siRNA compared to untreated cells (FIG. 4A).

To analyze the expression of some representative proteins, the amount of stat3 and p-stat3 at protein levels was measured in B16F10 cells treated with liposomal formulation of stat3siRNA and WP1066 using Western Blot experiments. Both the untreated cells and the treated cells were lysed and processed for immunoblotting with antibodies against stat3, p-stat3 and β-actin (control) as provided in FIG. 4B. Lane 1: untreated cells; lane 2: cells treated with stat3 siRNA (20 nM) encapsulated in liposome of CGKRK-lipopeptide 1; lane 3: cells treated with WP 1066 (2 µM) solubilized in liposome of CGKRK-lipopeptide 1; lane 4: cells treated with stat3 siRNA (20 nM) and WP1066 (2 µM) both co-encapsulated in liposome of CGKRK-lipopeptide 1; lane 5: cells treated with scrambled siRNA (20 nM) encapsulated in liposome of CGKRK-lipopeptide 1; lane 6: cells treated with scrambled siRNA (20 nM) and WP 1066 (2 µM) both co-encapsulated in liposome of CGKRK-lipopeptide 1. As observed, the level of p-stat3 protein was found to be significantly reduced in B16F10 cells treated with liposomal formulation of stat3siRNA and/or WP1066 compared to untreated cells.

To check the inhibition of stat3 phosphorylation in-vivo, the amount of stat3 and p-stat3 at protein level was measured in B16F10 cells treated with liposomal formulation of stat3siRNA and WP1066 using Western Blot experiments. Both the untreated cells and the treated cells were lysed and processed for immunoblotting with antibodies against p-stat3 as provided in FIG. 4C. Lane 1: untreated cells; lane 2: cells treated with stat3 siRNA (20 nM) encapsulated in liposome of CGKRK-lipopeptide 1; lane 3: cells treated with WP1066 (2 µM) solubilized in liposome of CGKRK-lipopeptide 1; lane 4: cells treated with stat3 siRNA (20 nM) and WP1066 (2 µM) both co-encapsulated in liposome of CGKRK-lipopeptide 1; lane 5: cells treated with scrambled siRNA (20 nM) encapsulated in liposome of CGKRK-lipopeptide 1; lane 6: cells treated with scrambled siRNA (20 nM) and WP1066 (2 µM) both co-encapsulated in liposome of CGKRK-lipopeptide 1. As observed, there was a decrease in p-stat3 protein level in B16F10 cells isolated from tumors treated with stat3-siRNA and/or WP1066 co-encapsulated in liposomes of CGKRK-lipopeptide 1 when compared to its level in tumor cells from untreated mice (FIG. 4C).

It was evident that treatment with liposomally co-encapsulated combination of chemotherapeutics was more potent in inhibiting stat3 signaling pathways at both mRNA and protein level when compared to their level in cells treated with liposomal formulation of single therapeutic agent. Moreover, liposomally encapsulated scrambled siRNA showed no effect in stat3 signalling pathway.

Example 7

Synergy Between Targeted Chemotherapy & Genetic Immunization Regresses Established Melanoma Tumor in Syngeneic Mouse Tumor Model B16F10 melanoma cells were harvested from T25 culture flasks using 1 mL cell dissociation solution (Sigma, USA), washed with PBS (2×200 µL) and resuspended in HBSS. ~1.8×10$^5$ B16F10 melanoma cells in 100 µL HBSS were subcutaneously injected in the right flank of 6-8 weeks old female C57BL/6J mice (each weighing 20-22 g) on day 0. Mice were then randomly sorted into three groups (n=5 for each group). The first group was administered intravenously with stat3 siRNA (2 µg/mice) and WP1066 (10 mg/kg B.W of mice) both co-encapsulated in liposomes of CGKRK-lipopeptide 1 on day 14, 16, 19, 21 and 24. The second group was not treated with liposomal formulation of WP1066 and STAT3siRNA but was only immunized. Both 1$^{st}$ and 2$^{nd}$ groups were immunized with electrostatic complexe of melanoma antigen encoded DNA vaccine (p-CMV-MART1) and direct in-vivo DC-targeting liposome on day 15 and 17 (using 200 µL 5% glucose solution containing 15 µg DNA, 4:1 lipid:DNA ratio for each mice). The third group (n=5) was intravenously injected with vehicle (5% aqueous glucose) alone. Tumor volumes (V=½·ab$^2$ where, a=maximum length of the tumor and b=minimum length of the tumor measured perpendicular to each other) were measured with a slide calipers.

Figure 5A:
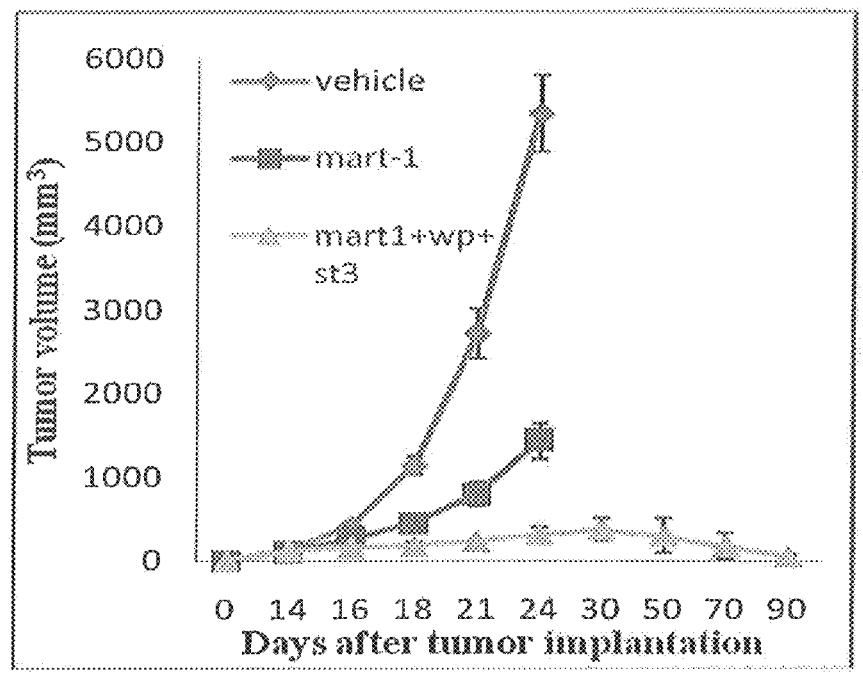
FIGS. 5A-5B show that combined effects of targeted chemotherapy and cancer immunotherapy not only increase survival rate of tumor bearing mice but also leads to complete regression of established tumor.
Figure 5B:
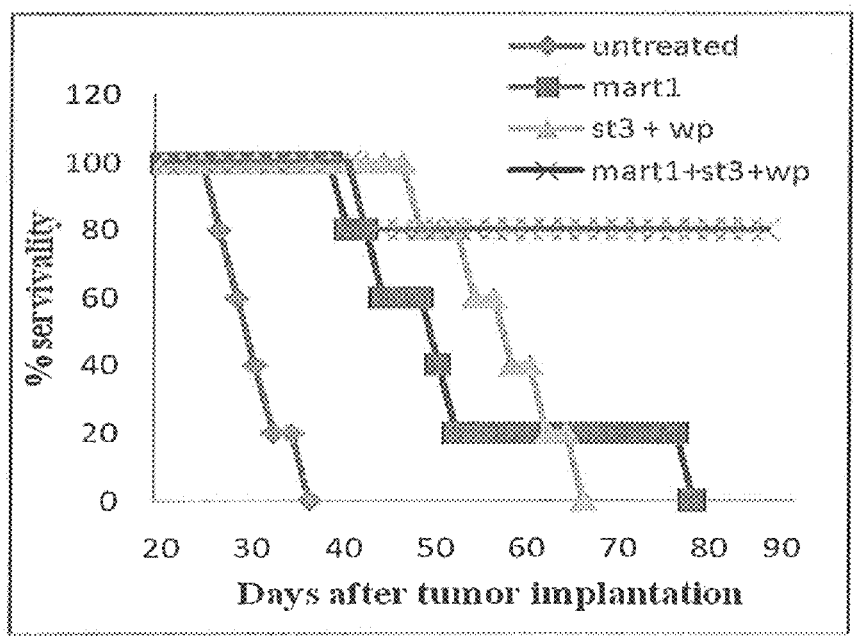

The results obtained for in-vivo tumor regression studies is provided in FIG. 5. FIG. 5A shows the regression of established tumor through combined use of targeted chemotherapy and genetic immunization and FIG. 5B shows the survivability study. Tumor growth inhibition studies (as provide in FIG. 5A) suggest that only genetic immunization (i.e. without using chemotherapeutic in combination with DNA vaccine) is not capable of regressing established tumor growth. Importantly, targeted intravenous administration of stat3 siRNA (2 µg/mice) and WP1066 (10 mg/kg B.W of mice) co-encapsulated in liposomes of CGKRK-lipopeptide of the present invention on day 14, 16, 19, 21 and 24 post tumor inoculation in combination with subcutaneous genetic immunization with lipoplexes of the melanoma antigen encoded DNA vaccine (p-CMV-MART1) in complexation with direct in-vivo mouse DCs targeting liposomes was capable of providing essentially complete regression of even established tumor (FIG. 5A) thereby demonstrating the remarkable therapeutic potential of such combination therapy in combating cancer.

ADVANTAGES OF THE INVENTION

The process of the present invention can be exploited for preparing cationic lipopeptide with integrin targeting peptide head group and for delivering biologically active compounds such as DNA, RNA, potent cytotoxic drugs, proteins etc. into both tumor endothelial cells and tumor cells. The present inventions are particularly useful for integrin receptor specific delivery of polyanions, polypeptides or nucleopolymers into tumor endothelial cells and tumor cells. The present invention is directed towards method to inhibit tumor growth via inhibiting stat3 phosphorylation by targeted delivery of stat3 siRNA and/or stat3 inhibitor (WP1066) into tumor vasculatures. The present invention demonstrates the dramatic therapeutic potential of using potent chemotherapeutic in combination. The present invention discloses the methods for regressing established tumors by simultaneous use of targeted chemotherapy and cancer immunotherapy. Furthermore, the present invention discloses that stat3 blockade can be synergized with other promising cancer immunotherapeutic modalities such as direct in-vivo targeting of DNA vaccine targeting to APCs via mannose receptor. The present invention describes a unique method of simultaneous use of targeted chemotherapy and cancer immunotherapy for regressing established tumor. The present invention disclose method of harnessing antitumor effects by a combination of targeted chemotherapy and genetic immunization in therapeutic mode (unlike commonly used preventive mode of DNA vaccination) i.e. by immunizing mice two weeks post tumor inoculation) with electrostatic complexes (lipoplexes) of DNA vaccines encoding melanoma tumor antigen Mart1(p-CMV-Mart1) and direct in-vivo DC-targeting cationic liposomes. The findings disclosed in the present invention avoid the needs of: (a) toxic side effects of single chemotherapeutics; (b) painstaking isolation of autologous DCs in genetic immunization; (c) ex-vivo transfection of the isolated DCs with DNA vaccines and the reimplantation of the ex vivo transfected DCs; and (d) non-specific delivery of chemotherapeutics to other organs such as liver, spleen, kidney etc. Taken together, the liposomal formulation of the present invention can regress established tumor through combined use of targeted chemotherapy and direct in-vivo stimulation of immune systems against growing tumor.

We claim:

1. A cationic lipopeptide having formula A

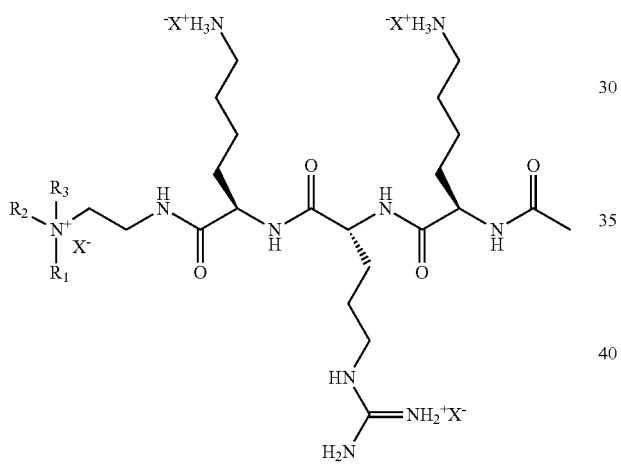

Formula A

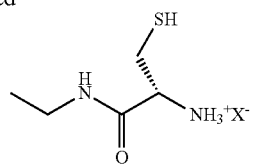

wherein, the sequence of the peptide is CGKRK; $R_1$ and $R_2$ are each independently selected from hydrogen or a lipophilic moiety containing eight to twenty four carbon atom selected from the group consisting of alkyl, mono-, di- and tri-unsaturated alkenyl, provided both $R_1$ and $R_2$ are not hydrogen;

$R_3$ is selected from a group consisting of hydrogen, $C_1$-$C_5$ alkyl, hydroxyl, and $C_1$-$C_5$ amino-alkyl; and X is either chlorine or bromine.

2. The cationic lipopeptide having formula A represented by cationic CGKRK-lipopeptide 1

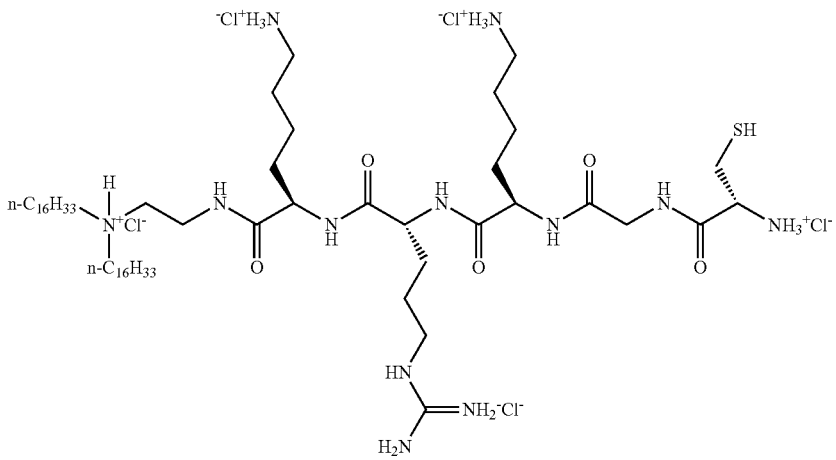

Cationic CGKRK-lipopeptide 1

3. A liposomal formulation comprising the cationic CGKRK-lipopeptide having formula A, at least one chemotherapeutic agent, at least two co-lipids and a pharmaceutically acceptable carrier

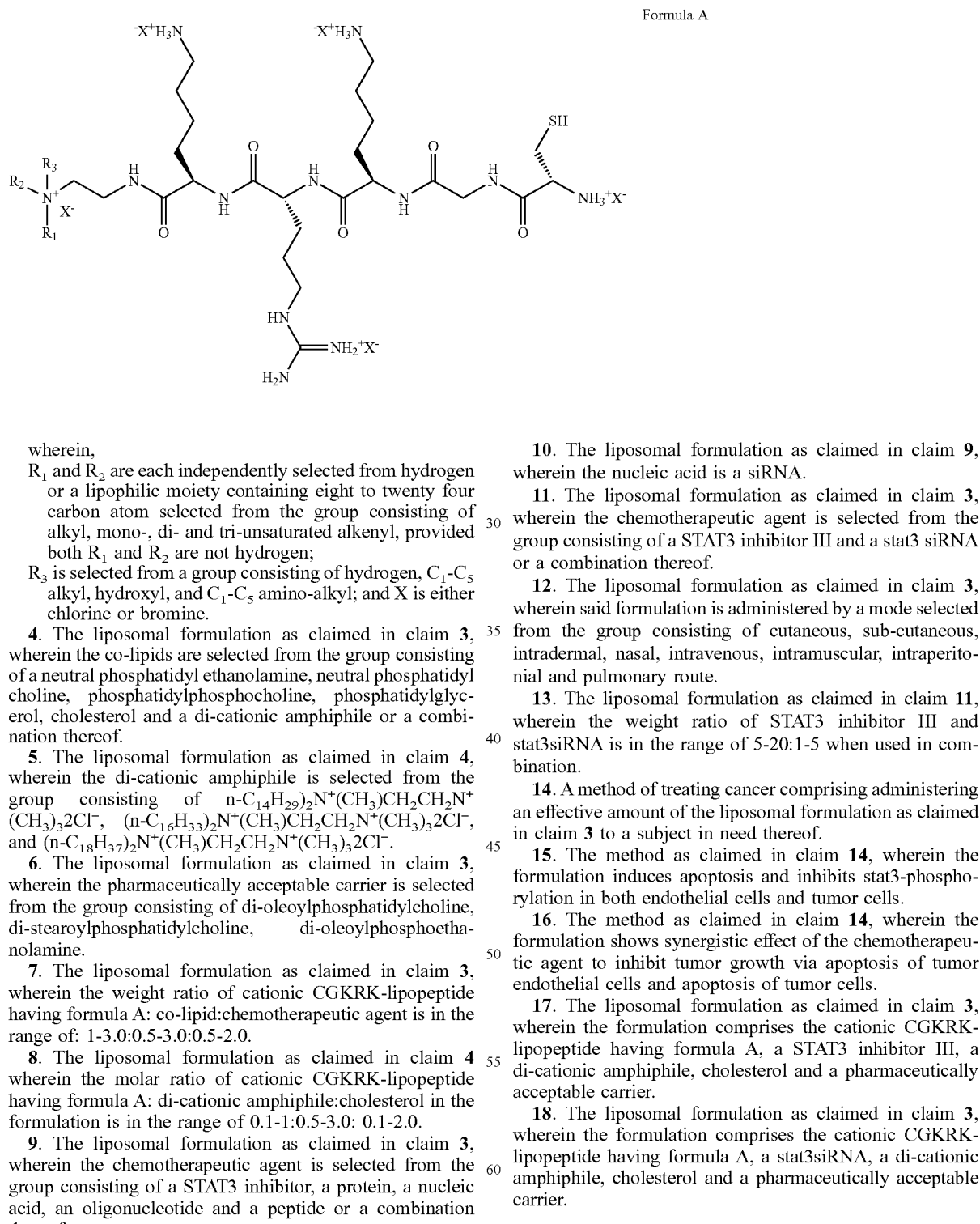

Formula A wherein, $R_1$ and $R_2$ are each independently selected from hydrogen or a lipophilic moiety containing eight to twenty four carbon atom selected from the group consisting of alkyl, mono-, di- and tri-unsaturated alkenyl, provided both $R_1$ and $R_2$ are not hydrogen;

$R_3$ is selected from a group consisting of hydrogen, $C_1$-$C_5$ alkyl, hydroxyl, and $C_1$-$C_5$ amino-alkyl; and X is either chlorine or bromine.

4. The liposomal formulation as claimed in claim 3, wherein the co-lipids are selected from the group consisting of a neutral phosphatidyl ethanolamine, neutral phosphatidyl choline, phosphatidylphosphocholine, phosphatidylglycerol, cholesterol and a di-cationic amphiphile or a combination thereof.

5. The liposomal formulation as claimed in claim 4, wherein the di-cationic amphiphile is selected from the group consisting of n-$C_{14}H_{29})_2N^+(CH_3)CH_2CH_2N^+(CH_3)_3 2Cl^-$, (n-$C_{16}H_{33})_2N^+(CH_3)CH_2CH_2N^+(CH_3)_3 2Cl^-$, and (n-$C_{18}H_{37})_2N^+(CH_3)CH_2CH_2N^+(CH_3)_3 2Cl^-$.

6. The liposomal formulation as claimed in claim 3, wherein the pharmaceutically acceptable carrier is selected from the group consisting of di-oleoylphosphatidylcholine, di-stearoylphosphatidylcholine, di-oleoylphosphoethanolamine.

7. The liposomal formulation as claimed in claim 3, wherein the weight ratio of cationic CGKRK-lipopeptide having formula A: co-lipid:chemotherapeutic agent is in the range of: 1-3.0:0.5-3.0:0.5-2.0.

8. The liposomal formulation as claimed in claim 4 wherein the molar ratio of cationic CGKRK-lipopeptide having formula A: di-cationic amphiphile:cholesterol in the formulation is in the range of 0.1-1:0.5-3.0: 0.1-2.0.

9. The liposomal formulation as claimed in claim 3, wherein the chemotherapeutic agent is selected from the group consisting of a STAT3 inhibitor, a protein, a nucleic acid, an oligonucleotide and a peptide or a combination thereof.

10. The liposomal formulation as claimed in claim 9, wherein the nucleic acid is a siRNA.

11. The liposomal formulation as claimed in claim 3, wherein the chemotherapeutic agent is selected from the group consisting of a STAT3 inhibitor III and a stat3 siRNA or a combination thereof.

12. The liposomal formulation as claimed in claim 3, wherein said formulation is administered by a mode selected from the group consisting of cutaneous, sub-cutaneous, intradermal, nasal, intravenous, intramuscular, intraperitonial and pulmonary route.

13. The liposomal formulation as claimed in claim 11, wherein the weight ratio of STAT3 inhibitor III and stat3siRNA is in the range of 5-20:1-5 when used in combination.

14. A method of treating cancer comprising administering an effective amount of the liposomal formulation as claimed in claim 3 to a subject in need thereof.

15. The method as claimed in claim 14, wherein the formulation induces apoptosis and inhibits stat3-phosphorylation in both endothelial cells and tumor cells.

16. The method as claimed in claim 14, wherein the formulation shows synergistic effect of the chemotherapeutic agent to inhibit tumor growth via apoptosis of tumor endothelial cells and apoptosis of tumor cells.

17. The liposomal formulation as claimed in claim 3, wherein the formulation comprises the cationic CGKRK-lipopeptide having formula A, a STAT3 inhibitor III, a di-cationic amphiphile, cholesterol and a pharmaceutically acceptable carrier.

18. The liposomal formulation as claimed in claim 3, wherein the formulation comprises the cationic CGKRK-lipopeptide having formula A, a stat3siRNA, a di-cationic amphiphile, cholesterol and a pharmaceutically acceptable carrier.

* * * * *